United States Patent
Murata et al.

(10) Patent No.: US 12,285,434 B2
(45) Date of Patent: Apr. 29, 2025

(54) THERAPEUTIC, PREVENTIVE, OR IMPROVEMENT AGENT FOR INFLAMMATORY DISEASE AND ALLERGIC DISEASE

(71) Applicant: The University of Tokyo, Tokyo (JP)

(72) Inventors: Takahisa Murata, Tokyo (JP); Tatsuro Nakamura, Tokyo (JP); Taiki Hamabata, Tokyo (JP); Kohei Ashina, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 958 days.

(21) Appl. No.: 17/414,559

(22) PCT Filed: Dec. 17, 2019

(86) PCT No.: PCT/JP2019/049500
§ 371 (c)(1),
(2) Date: Sep. 20, 2021

(87) PCT Pub. No.: WO2020/130003
PCT Pub. Date: Jun. 25, 2020

(65) Prior Publication Data
US 2022/0008435 A1 Jan. 13, 2022

(30) Foreign Application Priority Data
Dec. 17, 2018 (JP) .................................. 2018-235139

(51) Int. Cl.
*A61K 31/557* (2006.01)
*A23L 33/12* (2016.01)
(Continued)

(52) U.S. Cl.
CPC ............ *A61K 31/557* (2013.01); *A23L 33/12* (2016.08); *A61K 9/0019* (2013.01); *A61P 9/00* (2018.01); *A61P 37/08* (2018.01)

(58) Field of Classification Search
CPC .. A61K 31/557; A61K 9/0019; A61K 9/0014; A61K 9/0053; A61K 31/202;
(Continued)

(56) References Cited

U.S. PATENT DOCUMENTS

2002/0068712 A1* 6/2002 Stevens ................ C07K 14/705
514/44 A

OTHER PUBLICATIONS

Chiaro, Christopher R. et al., "Leukotriene A4 metabolites are endogenous ligands for the Ah receptor," Biochemistry, 2008, vol. 47, pp. 8445-8455.*
(Continued)

*Primary Examiner* — Deborah D Carr
(74) *Attorney, Agent, or Firm* — Hovey Williams LLP; Crissa Cook

(57) ABSTRACT

An object of the present invention is to provide a novel agent for treating, preventing or improving an inflammatory disease or an allergic disease. The present invention provides an agent for treating, preventing or improving an allergic disease, or as an agent for treating, preventing or improving an inflammatory disease or an allergic disease, comprising, as an active ingredient, (±) 5,6-dihydroxy-8Z,11Z,14Z,17Z-eicosatetraenoic acid (5,6-DiHETE). The inflammatory disease can be an inflammatory disease due to an increase of calcium concentration in vascular endothelial cells, and the inflammatory disease can be an inflammatory disease developed in a tissue or organ selected from the group consisting of digestive organs, circulatory organs, respiratory organs, urinary organs, genital organs, brain, skin, eyes, and fat.

17 Claims, 9 Drawing Sheets

(51) Int. Cl.
*A61K 9/00* (2006.01)
*A61P 9/00* (2006.01)
*A61P 37/08* (2006.01)

(58) Field of Classification Search
CPC .. A23L 33/12; A61P 9/00; A61P 37/08; A61P 1/04; A61P 11/06; A61P 29/00
See application file for complete search history.

(56) References Cited

OTHER PUBLICATIONS

Takamura, Takeyuki et al. Activation of aryl hydrocarbon receptor pathways and inflammatory bowel disease. Yamanashi Medical Journal., 2017, vol. 32, No. 1, pp. 7-13, abstract, p. 9, section 1).*
Beamer, Celine A. et al, "Role of the aryl hydrocarbon receptor (AhR) in lung inflammation," Seminars in Immunopathology, 2013, vol. 35, pp. 693-704.*
Tokuyama, Shogo et al. Present conditions and future prospects for unsaturated fatty acid as a new pain control material. Japanese Journal of Pharmaceutical Palliative Care and Sciences. n-3-type fatty acids.), vol. 4, 2011, pp. 45-51.*
Belluzzi, Andrea et al., "Polyunsaturated fatty acids and inflammatory bowel disease," American Journal of Clinical Nutrition, 2000, vol. 71, pp. 339S-342S.*
Hamabata, Taiki et al., "5, 6-DiHETE attenuates vascular hyperpermeability by inhibiting Ca2 + elevation in endothelial cells, " Journal of Lipid Research, 2018, vol. 59, pp. 18 64-1870.*

International Search Report and Written Opinion in corresponding PCT/JP2019/049500, dated Feb. 4, 2020 (English machine translation attached).
Chiaro, et al., "Leukotriene A4 Metabolites Are Endogenous Ligands for the Ah Receptor", Biochemistry, 2008, 47, pp. 8445-8455.
Takamura, et al., "Activation of Aryl hydrocarbon receptor pathway and inflammatory bowel disease", Yamanashi Medical Science Journal, 2017, 32(1), pp. 7-13 (English translation attached).
Beamer, et al., "Role of the aryl hydrocarbon receptor (AhR) in lung inflammation", Semin Immunopathol, 2013, 35 (6), pp. 693-704.
Tokuyama, et al., "Current Status and Future Prospects of Unsaturated Fatty Acids as New Pain Control Substances", Japan Journal of Palliative Medicine, 2011, 4, pp. 45-51 (English translation attached).
Belluzzi, et al., "Polyunsaturated fatty acids and inflammatory bowel disease", Am. J. Clin. Nutr., 2000, 71, pp. 339S-342S.
Hamabata, et al., "5,6-DiHETE attenuates vascular hyperpermeability by inhibiting Ca2+ elevation in endothelial cells", Journal of Lipid Research, 2018, 59, pp. 1864-1870.
Hamabata, et al., "Production of lipid mediators across different disease stages of dextran sodium sulfate-induced colitis in mice", Journal of Lipid Research, 2018, 59, pp. 586-595.
Medzhitov, "Origin and physiological roles of inflammation", Nature, 2008, vol. 454, pp. 428-435.
Hamabata, Proceedings of the 6th Shimadzu International Collaborative Laboratory Forum, 2018.

\* cited by examiner

THERAPEUTIC, PREVENTIVE, OR IMPROVEMENT AGENT FOR INFLAMMATORY DISEASE AND ALLERGIC DISEASE

REFERENCE TO RELATED APPLICATIONS

This application is the U.S. National Stage of International Patent Application No. PCT/JP2019/049500, filed Dec. 17, 2019, which claims the priority of Japanese Patent Application 2018-235139 (filed: Dec. 17, 2018), which is a prior Japanese patent application, the entire disclosures of which are incorporated herein by reference.

TECHNICAL FIELD

The present invention relates to an agent for treating, preventing or improving an inflammatory disease and an allergic disease.

TECHNICAL FIELD

Inflammation is a local biological defense reaction induced, for example, by bacterial/viral infection or trauma. In normal inflammation (acute inflammation), the stimulated microcirculatory system contracts transiently and then expands, and normally-closed capillary beds open, so that the blood flow increases. Furthermore, the formation of gaps between endothelial cells in the venular region causes a phenomenon of vascular hyperpermeability in which the plasma component exudes into the tissue stroma through the gaps. The vascular hyperpermeability usually occurs biphasically. In the first phase, a weak reaction is caused by prostaglandin, histamine, or serotonin, which is referred to as immediate permeability, and delayed permeability in the second phase constitutes the main vascular permeability in inflammation. Subsequently, multinuclear leukocytes, monocytes, lymphocytes, and the like advance from the venular region to the tissue stroma. The effect of the activator system produced by these plasma and cell components promotes proliferation of tissue cells, leading to repair (Non-Patent Document 1).

Many therapeutic agents have been developed because diseases involving an acute inflammatory response can be developed in various tissues and organs of living bodies. Of inflammatory diseases, inflammatory bowel disease (IBD) is a disease frequently found in developed countries, and the number of patients continues to increase also in Japan. The number of patients in Japan in 2014 is 170,000 for ulcerative colitis (10.1% year-on-year increase) and 40,000 for Crohn's disease (6.8% year-on-year increase). Inflammatory bowel disease is an intractable disease for which no cause has been identified, and new treatment strategies are still demanded.

REFERENCE LIST

Non-Patent Documents

Non-Patent Document 1: Medzhitov R., Nature, 454:428-435(2008)

SUMMARY OF THE INVENTION

An object of the present invention is to provide a novel agent for treating, preventing or improving an inflammatory disease. Another object of the present invention is to provide a novel agent for treating, preventing or improving an allergic disease.

The present inventors have now found that, in mice administered with (±) 5,6-dihydroxy-8Z,11Z,14Z,17Z-eicosatetraenoic acid (sometimes referred to as "5,6-DiHETE" herein), histamine-induced vascular dilation and vascular hyperpermeability are inhibited. The present inventors have also found that administration of 5,6-DiHETE inhibits acetylcholine-induced vascular relaxation and histamine-induced endothelial barrier dysfunction. The present inventors have also found that administration of 5,6-DiHETE inhibits histamine-induced increase of intracellular calcium ion concentration and subsequent nitric oxide (NO) production in human umbilical vein endothelial cells. The present inventors have also found that, in colitis mice in which colitis is induced upon administration of dextran sodium sulfate, the concentration of 5,6-DiHETE in the colon tissue increases during the healing phase of the induced colitis, and that administration of 5,6-DiHETE to the colitis mice inhibits formation of edema in the inflamed colon tissue and promotes healing of colitis. The present inventors have also found that, in pulmonary edema mice in which pulmonary edema is induced upon administration of hydrochloric acid, administration of 5,6-DiHETE inhibits formation of edema in the lung tissue. The present inventors have also found that, in anaphylaxis mice in which anaphylaxis is induced upon administration of histamine, administration of 5,6-DiHETE suppresses progression of anaphylaxis. The present inventors have also found that 5,6-DiHETE is abundant in the intestinal tract and liver of blue fish. The present invention is based on such findings.

According to the present invention, the following inventions are provided.

[1] An agent for treating, preventing, or improving an inflammatory disease and a composition for use in treating, preventing, or improving an inflammatory disease, each comprising, as an active ingredient, (±) 5,6-dihydroxy-8Z, 11Z,14Z,17Z-eicosatetraenoic acid (5,6-DiHETE).

[2] The agent and composition according to [1], wherein the inflammatory disease is a disease due to an increase of calcium concentration in vascular endothelial cells.

[3] The agent and composition according to [1] or [2], wherein the inflammatory disease is an inflammatory disease developed in a tissue or organ selected from the group consisting of digestive organs, circulatory organs, respiratory organs, urinary organs, genital organs, brain, skin, eyes, and fat.

[4] The agent and composition according to any one of [1] to [3], wherein the inflammatory disease is an inflammatory disease developed in the intestinal tract.

[5] The agent and composition according to [4], wherein the inflammatory disease developed in the intestinal tract is a disease selected from the group consisting of inflammatory bowel disease (IBD), irritable bowel syndrome (IBS) and infectious gastroenteritis.

[6] The agent and composition according to [5], wherein the inflammatory bowel disease (IBD) is a disease selected from the group consisting of ulcerative colitis, Crohn disease, enteric tuberculosis, ischemic colitis, radiation enterocolitis and drug-induced enteritis.

[7] The agent and composition according to any one of [1] to [3], wherein the inflammatory disease is an inflammatory disease developed in the lung.

[8] The agent and composition according to [7], wherein the inflammatory disease developed in the lung is a disease selected from the group consisting of pneumonia, pulmonary edema and fibroid lung.

[9] An agent for treating, preventing, or improving an allergic disease and a composition for use in treating, preventing or improving an allergic disease, each comprising, as an active ingredient, (±) 5,6-dihydroxy-8Z,11Z,14Z,17Z-eicosatetraenoic acid (5,6-DiHETE).

[10] The agent and composition according to [9], wherein the allergic disease is an allergic disease due to an increase of calcium concentration in vascular endothelial cells.

[11] The agent and composition according to [10], wherein the allergic disease is a disease selected from the group consisting of urticaria, allergic rhinitis, allergic conjunctivitis, atopic dermatitis, allergic gastroenteritis, food allergy, asthma, bronchial asthma, anaphylaxis and anaphylactic shock.

[12] The agent and composition according to any one of [1] to [11], which is in a dosage form selected from the group consisting of oral administration, percutaneous administration, and intravenous administration.

[13] A food for use in treatment, prevention, or improvement of an inflammatory disease, comprising, as an active ingredient, (±) 5,6-dihydroxy-8Z,11Z,14Z,17Z-eicosatetraenoic acid (5,6-DiHETE).

[14] A food for use in treatment, prevention, or improvement of an allergic disease, comprising, as an active ingredient, (±) 5,6-dihydroxy-8Z,11Z,14Z,17Z-eicosatetraenoic acid (5,6-DiHETE).

[15] The agent according to any one of [1] to [12] or the food according to [13] or [14], wherein the (±) 5,6-dihydroxy-8Z,11Z,14Z,17Z-eicosatetraenoic acid (5,6-DiHETE) is derived from a food.

[16] A method for treating, preventing, or improving an inflammatory disease, comprising administering an effective amount of (±) 5,6-dihydroxy-8Z,11Z,14Z,17Z-eicosatetraenoic acid (5,6-DiHETE) or a composition comprising the (±) 5,6-dihydroxy-8Z,11Z,14Z,17Z-eicosatetraenoic acid (5,6-DiHETE) to a subject in need thereof.

[17] A method for treating, preventing, or improving an allergic disease, comprising administering an effective amount of (±) 5,6-dihydroxy-8Z,11Z,14Z,17Z-eicosatetraenoic acid (5,6-DiHETE) or a composition comprising the (±) 5,6-dihydroxy-8Z,11Z,14Z,17Z-eicosatetraenoic acid (5,6-DiHETE) to a subject in need thereof.

[18] Use of (±) 5,6-dihydroxy-8Z,11Z,14Z,17Z-eicosatetraenoic acid (5,6-DiHETE), for the manufacture of an agent for treating, preventing, or improving an inflammatory disease, or as an agent for treating, preventing, or improving an inflammatory disease.

[19] Use of (±) 5,6-dihydroxy-8Z,11Z,14Z,17Z-eicosatetraenoic acid (5,6-DiHETE), for the manufacture of an agent for treating, preventing, or improving an allergic disease, or as an agent for treating, preventing, or improving an allergic disease.

[20] An agent for suppressing an increase of calcium concentration in vascular endothelial cells and a composition for use in suppressing an increase of calcium concentration in vascular endothelial cells, each comprising (±) 5,6-dihydroxy-8Z,11Z,14Z,17Z-eicosatetraenoic acid (5,6-DiHETE) as an active ingredient.

[21] An agent for reducing the risk of developing an inflammatory disease and a composition for use in reducing the risk of developing an inflammatory disease, each comprising, as an active ingredient, (±) 5,6-dihydroxy-8Z,11Z,14Z,17Z-eicosatetraenoic acid (5,6-DiHETE).

[22] An agent for reducing the risk of developing an allergic disease and a composition for use in reducing the risk of developing an allergic disease, each comprising, as an active ingredient, (±) 5,6-dihydroxy-8Z,11Z,14Z,17Z-eicosatetraenoic acid (5,6-DiHETE).

In the present specification, the agents according to the above [1], [9], [20], [21] and [22] are sometimes referred to as "the agents of the present invention," and the compositions according to the above [1], [9], [20], [21] and [22] are sometimes referred to as "the compositions of the present invention."

5,6-DiHETE, which is the active ingredient of the agents and compositions of the present invention, is a metabolite of omega-3 fatty acid which has been eaten by humans and is an endogenous substance. Therefore, according to the present invention, an agent for treating, preventing or improving an inflammatory disease, which has fewer side effects, can be provided.

Figure 1:
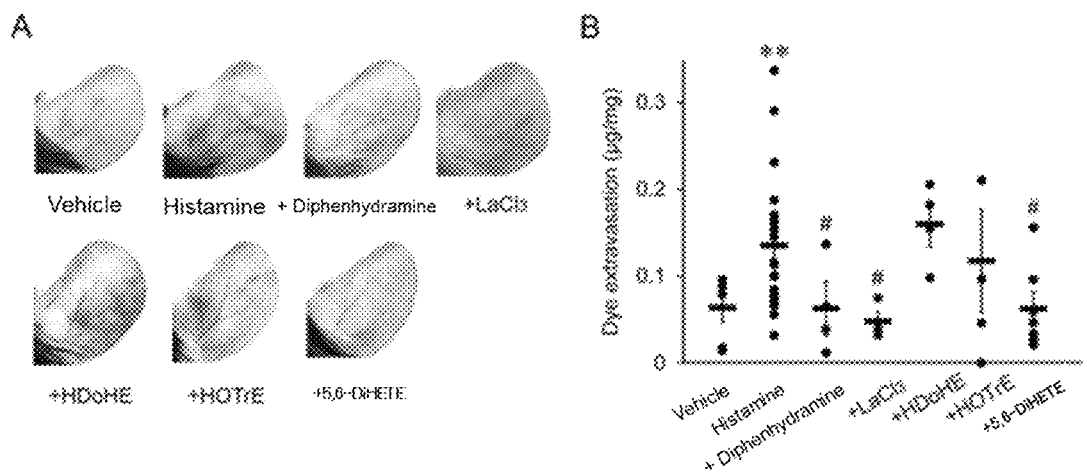
FIG. 1 shows an effect of 5,6-DiHETE on histamine-induced vascular hyperpermeability. (A) is a photograph showing effects of lipid metabolites on histamine-induced vascular permeability in mouse ears. (B) is a graph indicating quantified amounts of an extravasated dye (n=4 to 22). ** represents $P<0.01$ (relative to vehicle) and # represents $P<0.05$ (relative to histamine)

DETAILED DESCRIPTION OF THE INVENTION (±) 5,6-dihydroxy-8Z,11Z,14Z,17Z-eicosatetraenoic acid (CAS No. 845673-97-4), which is the active ingredient of the agents and compositions of the present invention, is an ω3 fatty acid metabolite produced from ω3 fatty acids such as eicosapentaenoic acid (EPA) and docosahexaenoic acid (DHA).

The chemical structural formula of 5,6-DiHETE (according to the relative arrangement (relative stereochemistry)) is as shown below.

[Chemical Formula 1]

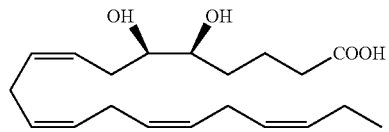

5,6-DiHETE can be prepared after metabolizing eicosapentaenoic acid with a cytochrome P450 catalyst and epoxidizing an α-5 double bond. Alternatively, commercially available 5,6-DiHETE may be used in the present invention.

According to the Examples which will be described below, it was confirmed that 5,6-DiHETE is abundant in blue fish. Therefore, 5,6-DiHETE, which is used in the agents and compositions of the present invention, can be prepared from natural materials and food materials such as plants and fish. For example, in the present invention, a preparation of blue fish can be used as 5,6-DiHETE. In the present invention, the blue fish used in the preparation of 5,6-DiHETE include fish of the order Clupeiformes, the family Carangidae (e.g., Japanese sardine (*Sardinops melanostictus*) and round herring (*Etrumeus micropus*)); the order Clupeiformes, the family Engraulidae (e.g., anchovy (*Engraulis japonica*)); the order Beloniformes, the family Scomberesocidae (e.g., saury (*Cololabis saira*)); the order Perciformes, the family Carangidae (e.g., horse mackerel (*Trachurus japonicus*)); and the order Perciformes, the family Scombridae (e.g., chub mackerel (*Scomber japonicus*) and blue mackerel (*Scomber australasicus*)). The site of blue fish used in the preparation of 5,6-DiHETE includes intestinal tract, liver, muscle, bone and heart, and is preferably intestinal tract and liver. 5,6-DiHETE can be prepared from blue fish, for example, by alcohol extraction. Therefore, in the agents and compositions of the present invention, an alcohol extract of blue fish can be used as 5,6-DiHETE. In addition, ω3 fatty acids such as a-linolenic acid, EPA and DHA can be metabolized in vivo, after ingestion, to produce 5,6-DiHETE. Therefore, in the agents and compositions of the present invention, ω3 fatty acids or natural materials and food materials containing them (for example, linseed oil, *perilla* oil and walnut) can be used as 5,6-DiHETE.

The agents and compositions of the present invention can use 5,6-DiHETE alone, or can use 5,6-DiHETE in combination with any other component. The content (in terms of solid content) of 5,6-DiHETE in the agents and compositions of the present invention can be arbitrarily determined according to the purpose, intended use, form and dosage form thereof, symptom, age, and the like, and can be, for example, 0.001 to 99% by mass or 0.01 to 95% by mass based on the total amount though the present invention is not limited thereto. In the present invention, the agents of the present invention may consist of 5,6-DiHETE, and the compositions of the present invention may contain 5,6-DiHETE and any other component.

The 5,6-DiHETE concentration can be measured, for example, by mass spectrometries and immunoassays such as ELISA and immunochromatography. Examples of mass spectrometry include liquid chromatography-mass spectrometry (LC-MS), liquid chromatography-tandem mass spectrometry (LC-MSMS), high-performance liquid chromatography-mass spectrometry (HPLC-MS), and high-performance liquid chromatography-tandem mass spectrometry (HPLC-MSMS) Immunoassays are analytical methods that use a detectably-labeled anti-lipid metabolite antibody or a detectably-labeled antibody (secondary antibody) against an anti-lipid metabolite antibody. Depending on the antibody labeling method, immunoassays are classified into enzyme immunoassay (EIA or ELISA), radioimmunoassay (RIA), fluorescence immunoassay (FIA), fluorescence polarization immunoassay (FPIA), chemiluminescence immunoassay (CLIA), and the like, all of which can be used in the present invention. From the viewpoint of accurate measurement of the concentrations of fatty acid metabolites which are similar in structure, measurement by mass spectrometries (particularly, LC-MSMS and HPLC-MSMS) are preferred.

The agents and compositions of the present invention are intended for use in treatment, prevention and/or improvement of an inflammatory disease. Here, the "inflammatory disease" is not particularly limited as long as it is a disease accompanied by inflammation (particularly, acute inflammation) developed in tissues and organs of living bodies, and includes diseases accompanied by inflammation developed in tissues and organs such as digestive organs (e.g., liver, digestive tract, and intestinal tract such as colon and small intestine), circulatory organs, respiratory organs (e.g., lung, oral cavity and nasal cavity), urinary organs (e.g., kidney and bladder), genital organs, brain, skin and eyes, and in the whole body. Preferably, the inflammatory disease is a disease accompanied by inflammation developed in the intestinal tract, skin, nasal cavity, oral cavity, lung, or whole body. Examples of the inflammatory disease developed in the intestinal tract include inflammatory bowel disease (IBD), irritable bowel syndrome (IBS) and infectious gastroenteritis. The inflammatory bowel disease (IBD) is a generic name for diseases causing chronic inflammation in mucosal membranes of the colon and the small intestine, and includes ulcerative colitis, Crohn disease, enteric tuberculosis, ischemic colitis, radiation enterocolitis and drug-induced enteritis. The inflammatory disease developed in the skin includes infectious diseases and allergic dermatitis. The inflammatory disease developed in the lung includes pneumonia, pulmonary edema and fibroid lung. The inflammatory disease also includes an allergic disease, which is an aspect of inflammation.

As a mechanism of inflammation, the following mechanism is known: an increase of intracellular calcium concentration in vascular endothelial cells induces nitric oxide production in the endothelial cells; and the induced nitric oxide causes relaxation of the vascular smooth muscle to cause vascular dilation, resulting in an increase in blood flow and disruption of the endothelial cell barrier function. Vascular hyperpermeability is caused by two main factors: disruption of the endothelial cell barrier function and increase in blood flow. This causes the inflammatory cells to be infiltrated into the tissue from the blood to enhance the inflammatory response. Excessive and/or sustained vascular hyperpermeability is known to trigger a variety of inflammatory diseases (Goel, S. et al., Physiological reviews, 91:1071-1121(2011), and Mehta, D. & A. B. Malik, Physiological reviews 86:279-367(2006)).

According to the Examples which will be described below, it was confirmed that 5,6-DiHETE inhibits a histamine-induced increase of vascular intracellular calcium concentration in human endothelial cells to suppress disruption of the endothelial cell barrier function, and suppresses vascular dilation caused by relaxation of the vascular smooth muscle, and therefore suppresses histamine-induced vascular hyperpermeability. Therefore, the agents and compositions of the present invention can be used to treat an inflammatory disease resulting from an increase of intracellular calcium concentration in vascular endothelial cells, among inflammatory diseases. Further, according to another aspect of the present invention, there are provided an agent for suppressing an increase of calcium concentration in vascular endothelial cells and a composition for use in suppressing an increase of calcium concentration in vascular endothelial cells, each comprising 5,6-DiHETE as an active ingredient.

Also, according to the Examples which will be described below, 5,6-DiHETE suppressed an anaphylaxis symptom, which is one of symptoms of an allergic disease. This is considered to be because 5,6-DiHETE inhibited a histamine-induced increase of vascular intracellular calcium concentration in human endothelial cells to suppress disruption of the endothelial cell barrier function and to suppress vascular dilation caused by relaxation of the vascular smooth muscle, thereby suppressing a blood pressure decrease and a body temperature decrease which are symptoms of anaphylactic reactions. Therefore, the agents and compositions of the present invention are used to treat, prevent and/or improve allergic diseases, and can be used to treat, particularly, allergic diseases due to an increase of intracellular calcium concentration in vascular endothelial cells (e.g., urticaria, allergic rhinitis, allergic conjunctivitis, atopic dermatitis, allergic gastroenteritis, food allergies, asthma, bronchial asthma, anaphylaxis, and anaphylactic shock), among allergic diseases.

The agents and compositions of the present invention can be provided in the form of pharmaceutical products (for example, pharmaceutical compositions), quasi-drugs (including medical cosmetic products), foods (for example, food compositions), feeds (including livestock feeds and pet foods), cosmetic products (for example, cosmetic compositions) and the like, and can be implemented according to the following description.

When the agents and compositions of the present invention are provided as pharmaceutical products, the route of administration is not particularly limited and may be either oral administration or parenteral administration (for example, percutaneous administration and intravenous administration). Examples of agents for oral administration include tablets, capsules, granules, powders, tablets (including sugar-coated tablets), pills, troche tablets, chewable tablets, candy-like agents, syrups, liquids, emulsions, suspensions, and jellies. Examples of agents for parenteral administration include injections, suppositories, inhalants, percutaneous absorbents, external preparations for skin, eye drops, and nasal drops. These formulations can be formed using a pharmaceutically acceptable carrier by a technique commonly used in the art (for example, a known method described in the Japanese Pharmacopoeia, 15th Edition, General Regulations for Preparations and the like). The pharmaceutically acceptable carrier includes excipients, binders, diluents, additives, perfumes, buffers, thickeners, colorants, stabilizers, emulsifiers, dispersants, suspending agents, and preservatives.

When the agents and compositions of the present invention are provided as foods, the foods containing 5,6-DiHETE can be provided. The foods provided in this manner are foods containing an effective amount of 5,6-DiHETE. As used herein, the phrase "containing an effective amount" of 5,6-DiHETE means a content of 5,6-DiHETE which would allow 5,6-DiHETE to be ingested by the subject in a range as will be described below, when used in an amount commonly used in individual foods. The "food" is used in the meaning including health foods, functional foods, dietary supplements, foods with health claims (for example, foods for specified health use, foods with nutrient function claims, and foods with functional claims), foods for special dietary uses (for example, foods for infants, foods for expectant and nursing mothers, and foods for sick persons), and supplements.

The form of the "food" is not particularly limited, and may be, for example, a liquid, semi-liquid or gel form, or a solid or powder form. The "supplement" includes tablets manufactured by adding an excipient and a binder to 5,6-DiHETE, kneading them, and then tableting the kneaded product, and capsule agents obtained by encapsulating 5,6-DiHETE together with an excipient and a binder.

The food provided in the present invention is not particularly limited as long as it contains an effective amount of 5,6-DiHETE, and includes beverages, processed vegetable products, processed fruit products, spices, noodles, breads, processed grain products, confectioneries, pulse products, meat products, dairy products, processed egg products, processed marine products, seasonings, edible oils and fats, cooked products, and semi-cooked foods. 5,6-DiHETE has an effect for improving an inflammatory disease and an allergic disease as described above, and thus is advantageous in that it can reduce the risk of developing inflammation and allergic reactions, and diseases associated therewith, when blended in foods which may induce or enhance inflammation and allergic reactions.

When the agents and compositions of the present invention are provided as cosmetic products, 5,6-DiHETE can be formulated and manufactured according to a conventional method using a base material, a carrier, an additive, a moisturizing ingredient, and the like, which are acceptable for cosmetic products. The cosmetic product of the present invention may also be prepared by blending 5,6-DiHETE with an existing cosmetic product. It can be produced according to a conventional method by blending 5,6-DiHETE together with a base material, a carrier, an additive, a moisturizing ingredient and the like which are conventionally acceptable for cosmetic products.

The dose of 5,6-DiHETE in the present invention can be determined depending on the sex, age and body weight of the subject to which 5,6-DiHETE is administered, symptoms, ingestion time, dosage form, administration route, drug to be combined, and the like. In the present invention, when 5,6-DiHETE is administered for the purpose of treating, preventing or improving an inflammatory disease or an allergic disease, the daily dose for humans can be set, for example, in the range of 1 to 1,000 mg, but is not limited thereto. The agents and compositions of the present invention can be administered not only to humans in need thereof, but also to non-human mammals (e.g., mice, rats, rabbits, dogs, cats, cows, horses, pigs, sheep, goats, and monkeys). The dose of 5,6-DiHETE described above is applicable when 5,6-DiHETE is used for both non-therapeutic and therapeutic purposes. In the case of non-therapeutic purposes, administration can be read as ingestion or application.

The agents and compositions of the present invention comprise, as an active ingredient, 5,6-DiHETE which is a metabolite of ω3 fatty acid having been eaten by humans, and thus, even when used continuously, have no concern about side effects and are highly safe. Therefore, when the agents and compositions of the present invention are used in combination with an existing anti-inflammatory agent or antiallergic agent, the dose of the existing agent can be reduced, and, therefore, the side effects of the existing agent can be reduced or eliminated. When combined with any other drug, the agents and compositions of the present invention may be prepared separately from the other drug, or blended together with any other drug in the same composition.

As shown in the Examples which will be described below, 5,6-DiHETE has an effect of suppressing an increase of calcium concentration in vascular endothelial cells, which induces an inflammatory response in vivo, and thus the agents and compositions of the present invention can be administered to a subject at risk of developing an inflammatory disease, thereby reducing the risk of developing an inflammatory disease. Here, the "subject at risk of developing an inflammatory disease" a subject who notices no symptoms of an inflammatory disease but is in danger of developing an inflammatory disease in the future. The "reducing the risk of developing an inflammatory disease" means that the probability of developing an inflammatory disease is reduced. That is, according to another aspect of the present invention, there are provided an agent for reducing the risk of developing an inflammatory disease and a composition for use in reducing the risk of developing an inflammatory disease, each comprising 5,6-DiHETE as an active ingredient.

As presented in the Examples which will be described below, 5,6-DiHETE has an effect of suppressing an anaphylactic reaction, which is a kind of allergic reaction, and thus the agents and compositions of the present invention can be administered to a subject at risk of developing an allergic disease, thereby reducing the risk of developing an allergic disease. Here, the "subject at risk of developing an allergic disease" means a subject who notices no symptoms of an allergic disease but is in danger of an allergic disease in the future. The "reducing the risk of developing an allergic disease" means that the probability of developing an allergic disease is reduced. That is, according to another aspect of the present invention, there are provided an agent for reducing the risk of developing an allergic disease and a composition for use in reducing the risk of developing an allergic disease, each comprising 5,6-DiHETE as an active ingredient.

According to another aspect of the present invention, there is provided a method for treating, preventing and/or improving an inflammatory disease, comprising administering an effective amount of 5,6-DiHETE of the present invention or a composition comprising the 5,6-DiHETE to a subject in need thereof. Also, according to another aspect of the present invention, there is provided a method for suppressing an increase of calcium concentration in vascular endothelial cells, comprising administering an effective amount of 5,6-DiHETE of the present invention or a composition comprising the 5,6-DiHETE to a subject in need thereof. Also, according to another aspect of the present invention, there is provided a method for reducing the risk of developing an inflammatory disease, comprising administering an effective amount of 5,6-DiHETE of the present invention or a composition comprising the 5,6-DiHETE to a subject in need thereof. The methods of the present invention can be carried out according to the descriptions regarding the agents and compositions of the present invention.

According to another aspect of the invention, there is provided a method for treating, preventing and improving an allergic disease, comprising administering an effective amount of 5,6-DiHETE of the present invention or a composition comprising the 5,6-DiHETE to a subject in need thereof. Also, according to another aspect of the present invention, there is provided a method for reducing the risk of developing an allergic disease, comprising administering an effective amount of 5,6-DiHETE of the present invention or a composition comprising the 5,6-DiHETE to a subject in need thereof. The methods of the present invention can be carried out according to the descriptions regarding the agents and compositions of the present invention.

According to another aspect of the invention, there is provided use of 5,6-DiHETE, for the manufacture of an agent for treating, preventing and/or improving an inflammatory disease, or as an agent for treating, preventing and/or improving an inflammatory disease. Further, according to another aspect of the present invention, there is provided use of 5,6-DiHETE, for the manufacture of an agent for suppressing an increase of calcium concentration in vascular endothelial cells or as an agent for suppressing an increase of calcium concentration in vascular endothelial cells. Also, according to another aspect of the present invention, there is provided use of 5,6-DiHETE, for the manufacture of an agent for reducing the risk of developing an inflammatory disease, or as an agent for reducing the risk of developing an inflammatory disease. The uses of the present invention can be carried out according to the descriptions regarding the agents and compositions of the present invention.

According to another aspect of the invention, there is provided use of 5,6-DiHETE, for the manufacture of an agent for treating, preventing and/or improving an allergic disease, or as an agent for treating, preventing and/or improving an allergic disease. Also, according to another aspect of the present invention, there is provided use of 5,6-DiHETE, for the manufacture of an agent for reducing the risk of developing an allergic disease, or as an agent for reducing the risk of developing an allergic disease. The uses of the present invention can be carried out according to the descriptions regarding the agents and compositions of the present invention.

According to another aspect of the invention, there is provided 5,6-DiHETE, as a medicament for treating, preventing and/or improving an inflammatory disease, or for use in treatment, prevention and/or improvement of an inflammatory disease. Also, according to another aspect of the present invention, there is provided 5,6-DiHETE for use in suppression of an increase of calcium concentration in vascular endothelial cells. Also, according to another aspect of the invention, there is provided 5,6-DiHETE for use in reduction of the risk of developing an inflammatory disease. The 5,6-DiHETE of the present invention can be carried out according to the descriptions regarding the agents and compositions of the present invention.

According to another aspect of the present invention, there is provided 5,6-DiHETE, as a medicament for treating, preventing and/or improving an allergic disease, or for use in treatment, prevention and/or improvement of an allergic disease. Also, according to another aspect of the invention, there is provided 5,6-DiHETE for use in reducing the risk of developing an allergic disease. The 5,6-DiHETE of the present invention can be carried out according to the descriptions regarding the agents and compositions of the present invention.

The methods of the present invention and the uses of the present invention may be uses in mammals including humans, and are intended to involve both of therapeutic use and non-therapeutic use. The "non-therapeutic," as used herein, means elimination of operating, treating or diagnosing activities to a human (i.e., medical activities to a human), and specifically means elimination of a method of performing operation or treatment of, or diagnosis involving, a human by a doctor or a person who receives an instruction from the doctor.

EXAMPLES

Hereinafter, the present invention will be described in more detail by way of the following examples, but is not limited thereto.

Example 1: Inhibitory Effect of 5,6-DiHETE on Histamine-Induced Vascular Hyperpermeability (1) Modified Miles Assay C57BL/6 strain mice (male, 8 to 12 weeks old) were injected intracutaneously, as pretreatment, with diphenhydramine (2.5 µg, manufactured by Molecular Probes), $LaCl_3$ (250 µg), 7-HDoHE (0.1 µg, manufactured by Cayman Chemical), 13-HOTrE (0.1 µg, manufactured by Cayman Chemical) or 5,6-DiHETE (0.1 µg, manufactured by Cayman Chemical). Fifteen (15) minutes after the intracutaneous injection, a vehicle (80% acetone) or histamine (400 µg, manufactured by Molecular Probes) was percutaneously administered to the ventral surface of the ears. To evaluate vascular permeability, Evans blue (50 mg/kg, manufactured by Sigma) was injected intravenously 5 minutes after the administration of histamine. The mice were then euthanized by cervical dislocation 30 minutes after the injection of Evans blue. The ears were dissected, dried at 55° C., and weighed. Extravasated Evans blue present in the ears was extracted in formamide (manufactured by Molecular Probes), and quantified spectrophotometrically (manufactured by PerkinElmer Japan Co., Ltd.) at a wavelength of 610 nm.

(2) Statistical Processing

In Examples 1 to 6, the measured values were expressed as mean±standard error (SEM). The data was statistically evaluated using one-way ANOVA, followed by Bonferroni's test for comparison among three or more groups. When $p<0.05$, there was decided to be a statistically significant difference.

(3) Results

The results were as shown in FIG. 1.

From the results shown in FIG. 1, the administration of 400 μg histamine induced blue dye extravasation (0.14±0.02 μg/mg). This amount was twice the amount of blue dye extravasated by the vehicle treatment (0.06±0.02 μg). Histamine stimulates a histamine H1 receptor to increase the intracellular calcium ion concentration ($[Ca^{2+}]_i$) in endothelial cells. This signaling activation promotes endothelial NO production, which in turn causes vascular dilation and vascular hyperpermeability. Pretreatment with the histamine H1 receptor blocker diphenhydramine (2.5 μg/ear, 15 minutes) or a calcium ion channel blocker $LaCl_3$ (250 μg/ear, 15 minutes) significantly inhibited dye extravasation. Also, pretreatment with 7-HDoHE (0.1 μg/ear, 15 minutes) or 13-HOTrE (0.1 μg/ear, 15 minutes) did not affect histamine-induced dye extravasation in the mouse ears. In contrast, pretreatment with 5,6-DiHETE (0.1 μg/ear, 15 minutes) significantly inhibited dye extravasation (0.06±0.02 μg/mg). The above results demonstrated that 5,6-DiHETE inhibits vascular hyperpermeability in vivo.

Example 2: Inhibitory Effect of 5,6-DiHETE on Histamine-Induced Arterial Relaxation (1) In Vivo Microscopy To visualize the ear vessels of the mice, 70 kDa fluorescein isothiocyanate-dextran (10 mg/kg, manufactured by Sigma-Aldrich) was injected intravenously. Then, immediately after the administration of fluorescein isothiocyanate-dextran, 5,6-DiHETE (0.1 μg) was administered by instillation (percutaneously administered) as a pretreatment, and this group of mice was designated as a "5,6-DiHETE-administered group." As a control group, a group of mice not administered with 5,6-DiHETE was designated as a "histamine-administered group". Then, 15 minutes after the administration by instillation, histamine (400 μg) was administered by instillation (percutaneously administered) into the ventral surface of the ears for both the groups. Next, the mice were placed on the stage of a microscope confocal microscope (ECLIPSE Ti with C1 confocal system, manufactured by Nikon Corporation), and their body temperatures were maintained at 37° C. Dextran leakage and vascular diameter in the ears were monitored every minute in a period from 0 to 30 minutes after the administration of histamine using EZ-C1 Free Viewer (manufactured by Nikon Corporation), and the dextran leakage, artery diameter and vein diameter were quantified according to the description of Omori, K. et al., British Journal of Pharmacology, 171:4879-4889 (2014). It is known that smooth muscle contraction reduces the downstream blood flow and limits the vascular leakage, whereas smooth muscle relaxation (increase of vascular diameter) increases the blood flow, thereby leading to vascular leakage.

(2) Results

Figure 2:
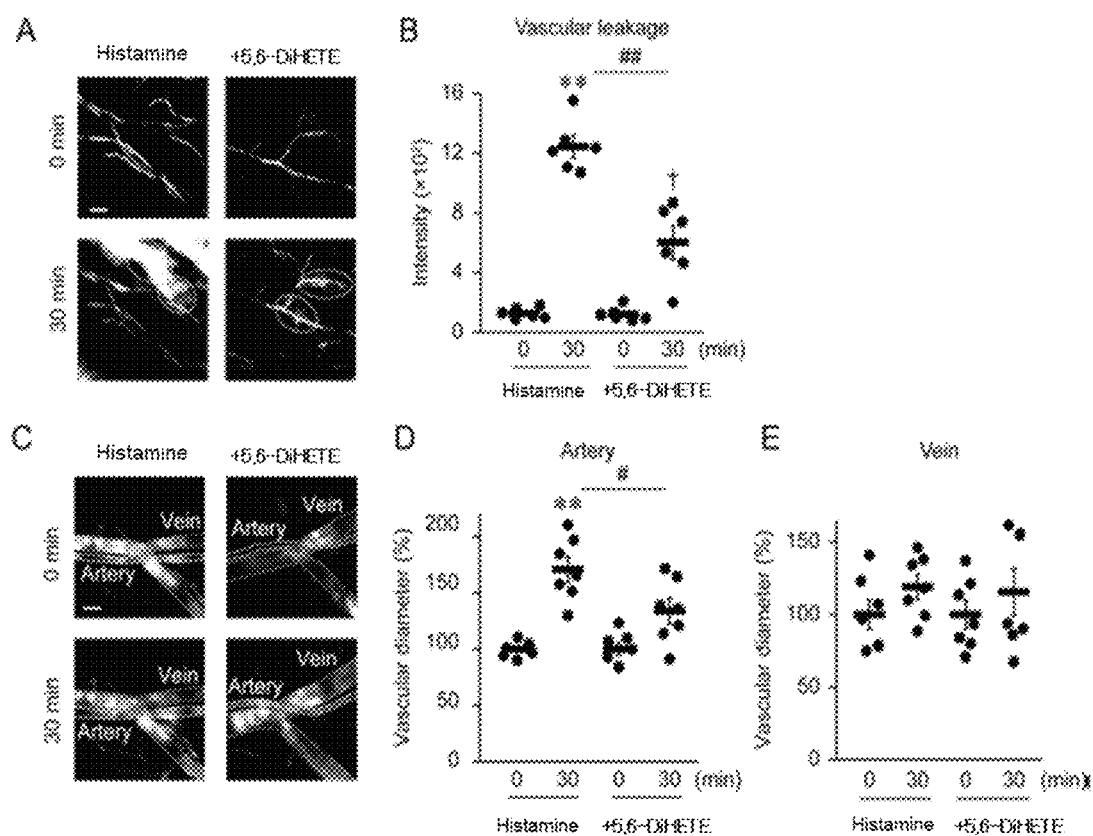
FIG. 2 shows an effect of 5,6-DiHETE on histamine-induced arterial relaxation and vascular hyperpermeability. (A) is a photograph showing an effect of 5,6-DiHETE on vascular hyperpermeability in a mouse ear. (B) is a graph indicating quantified extravasation of FITC-dextran (n=6 to 7). (C) is a photograph showing an effect of 5,6-DiHETE on arterial relaxation in the mouse ear. (D) is a graph indicating quantified artery diameters (n=6 to 7). (E) is a graph indicating quantified vein diameters (n=6 to 7).

The results were as shown in FIG. 2.

From the results shown in FIGS. 2A and 2B, in the histamine-administered group, extravasation of FITC-dextran was induced mainly from the bifurcation areas of the vasculature and peripheral blood vessels, and the mean fluorescence intensity of FITC-dextran was significantly higher at 30 minutes after the administration than that at 0 minutes after the administration of histamine. In the 5,6-DiHETE-administered group, the area of FITC-dextran extravasation was narrowed, and the mean fluorescence intensity was significantly decreased as compared with that of the samples for the histamine-administered group. From the results shown in FIGS. 2C and 2D, it was confirmed that histamine induced vascular dilation, from the fact that the artery diameter increased to 178±13% in the histamine-administered group as compared with that of arteries nonstimulated with histamine. In the 5,6-DiHETE-administered group, the artery diameter was 132±15% as compared with that of arteries nonstimulated with histamine, and the histamine-induced vascular dilation was significantly inhibited. On the other hand, the histamine-administered group tended to show an increase of vein diameter, but the histamine-induced increase of vein diameter was not inhibited in the 5,6-DiHETE-administered group.

Example 3: Inhibitory Effect of 5,6-DiHETE on Acetylcholine-Induced Aortic Relaxation (1) Measurement of Vascular Contraction of Aorta After excision of the thoracic aortae from untreated mice and removal of fat and connective tissue, the aortae were cut into rings to prepare aortic ring specimens. The ring specimens were immersed in a liquid tank filled with a normal nutrient solution (physiological saline solution containing 136.9 mM NaCl, 5.4 mM KCl, 5.5 mM glucose, 23.8 mM $NaHCO_3$, 1.5 mM $CaCl_2$, 1.0 mM $MgCl_2$ and 0.01 mM EDTA), and two stainless hooks were penetrated through the lumens of the ring specimens. One end of each of the stainless hooks was fixed, and the other end thereof was connected to a force-displacement transducer (T7-30-240, manufactured by Orientec Co., Ltd.) connected to a strain amplifier (3134 strain AMPL, manufactured by Yokogawa Test & Measurement Corporation). Then, the following operation (a), (b) or (c) was performed.

(a) Norepinephrine (manufactured by Sigma) was cumulatively added into the liquid tank containing the ring specimens after stabilization of each contraction (every about 30 minutes) so as to attain 0.001 μM, 0.01 μM, 0.1 μM and 1 μM, and this group was designated as a "norepinephrine-administered group" (n=4) (FIG. 3A). 5,6-DiHETE was cumulatively added into the liquid tank containing the ring specimen after stabilization of each contraction (every about 30 minutes) so as to attain 0.001 μM, 0.01 μM, 0.1 μM and 1 μM, and this group was designated as a "5,6-DiHETE-administered group" (n=4) (FIG. 3A).

(b) Norepinephrine was added into the liquid tank containing the ring specimens so as to attain 0.3 μM, and precontraction was induced by administration of norepinephrine (FIG. 3B). Then, after the contraction by the administration of norepinephrine was stabilized, acetylcholine (manufactured by Sigma) was cumulatively added after stabilization of each relaxation reaction (every about 15 minutes) so as to attain 0.03 µM, 0.1 µM, 0.3 µM and 1 µM, and this group was designated as an "acetylcholine-administered group" (FIG. 3B). After the contraction by the administration of norepinephrine was stabilized, 5,6-DiHETE was cumulatively added every about 15 minutes so as to attain 0.001 µM, 0.01 µM, 0.1 µM and 1 µM, and this group was designated as a "5,6-DiHETE-administered group" (n=4) (FIG. 3B).

(c) In order to verify the effect of 5,6-DiHETE on the acetylcholine administration, norepinephrine was added into the liquid tank containing the ring specimens so as to attain 1 µM. After the contraction by the administration of norepinephrine was stabilized, 5,6-DiHETE or a vehicle (solvent alone) was added so as to attain 1 µM. Then, acetylcholine was cumulatively administered (every about 15 minutes) after stabilization of each relaxation reaction so as to attain 0.03 µM, 0.1 µM, 0.3 µM and 1 µM, these groups were designated as "5,6-DiHETE-administered group" and "vehicle-administered group", respectively (FIG. 3C).

In the above operations (a) to (c), tension (contractile force) generated in the aortic ring specimens was measured isometrically over time using the above force-displacement transducer under a resting tension of 3 mN, and recorded.

(2) Results

Figure 3:
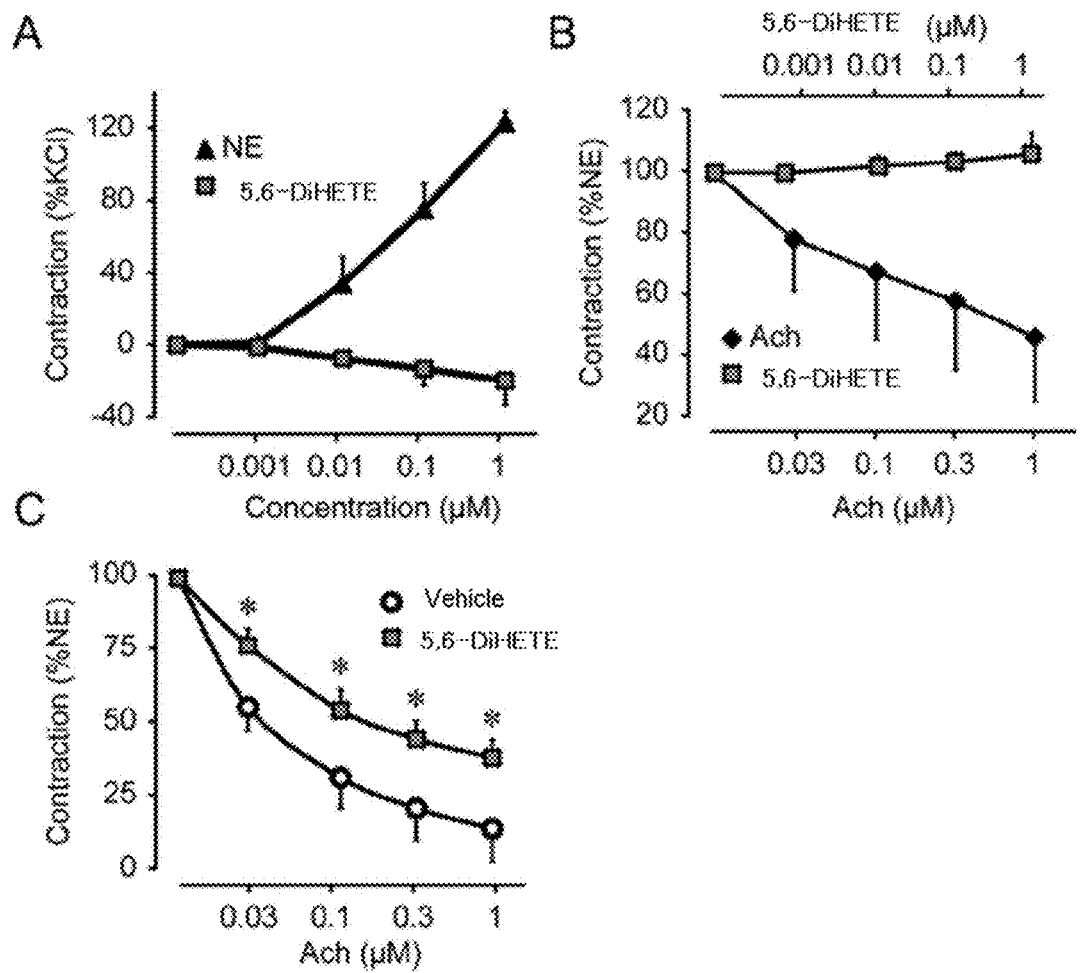
FIG. 3 shows an effect of 5,6-DiHETE on acetylcholine-induced aortic relaxation. (A) is a graph indicating an effect of cumulative administration of norepinephrine (NE) or 5,6-DiHETE on the aorta (n=4). (B) is a graph indicating an effect of cumulative administration of acetylcholine (Ach) or 5,6-DiHETE on the aorta precontracted by norepinephrine (n=4). (C) is a graph indicating an effect of pretreatment with 5,6-DiHETE on acetylcholine (Ach)-induced relaxation of the aorta precontracted by norepinephrine (n=9).

The results were as shown in FIG. 3.

From the results shown in FIG. 3A, the aortae were contracted in a concentration-dependent manner in the norepinephrine-administered group, but, in contrast, no contraction was caused in the 5,6-DiHETE-administered group. From the results shown in FIG. 3B, acetylcholine dilated, in a dose-dependent manner, the mouse aortae precontracted by norepinephrine, whereas 5,6-DiHETE did not affect the precontraction by norepinephrine. From the results shown in FIG. 3C, acetylcholine-induced aortic relaxation was significantly attenuated in the 5,6-DiHETE-administered group, as compared with that in the vehicle-administered group. The above results demonstrated that 5,6-DiHETE suppresses acetylcholine-induced smooth muscle relaxation without affecting smooth muscle contraction in arteries.

Example 4: Inhibitory Effect of 5,6-DiHETE on Histamine-Induced Endothelial Barrier Dysfunction (1) Culture of Human Umbilical Vein Endothelial Cells In Examples 4 to 6, human umbilical vein endothelial cells (hereinafter, sometimes referred to as "HUVECs", manufactured by Lonza) were cultured in EGM-2 (manufactured by Lonza K.K.). These cells (passages 4 to 9) were used for experiments after 4-hour starvation in EBM-2 (manufactured by Lonza K.K.) containing 2% FBS.

(2) Evaluation of Endothelial Barrier Function

The in vitro endothelial barrier function was evaluated by measuring the transendothelial electrical resistance (hereinafter, sometimes referred to as "TER") of the HUVECs prepared in the above item (1) over time. Specifically, the transendothelial electrical resistance was measured using an xCELLigence Real-Time Cell Analyzer DP system (manufactured by Roche). The system monitors changes in TER across an interdigitated microelectrode at the bottom of tissue culture E-plates (manufactured by Roche). The HUVECs (8,000 cells) were plated on the E-plates and incubated until confluent. Then, the following operation (a) or (b) was performed.

(a) Each reagent was added to plates on which the HUVECs were cultured, so as to give a vehicle, 1 U/mL thrombin, 1 µM forskolin, or 0.1 µM or 0.3 µM 5,6-DiHETE (FIGS. 4A and 4B).

(b) A vehicle or histamine was added to plates on which the HUVECs were cultured, so as to attain 10 µM. Alternatively, 30 minutes before the administration (addition) of histamine, each reagent was added to plates on which the HUVECs were cultured, so as to give 10 µM diphenhydramine, 0.1 µM 5,6-DiHETE, or 0.3 µM 5,6-DiHETE. Thirty (30) minutes after the addition, 10 µM histamine was added to each plate 30 minutes after the addition (FIGS. 4C and 4D).

In the above operations (a) and (b), the TER was measured every 60 seconds. For normalization, the cell index value at each time point is shown as a ratio relative to the initial value. The maximum normalized cell index after stimulation was quantified and represented as maximal response. Note that it is known that the disruption of the endothelial barrier function lowers the TER, but that the enhancement of the endothelial barrier function increases the TER.

(3) Results

Figure 4:
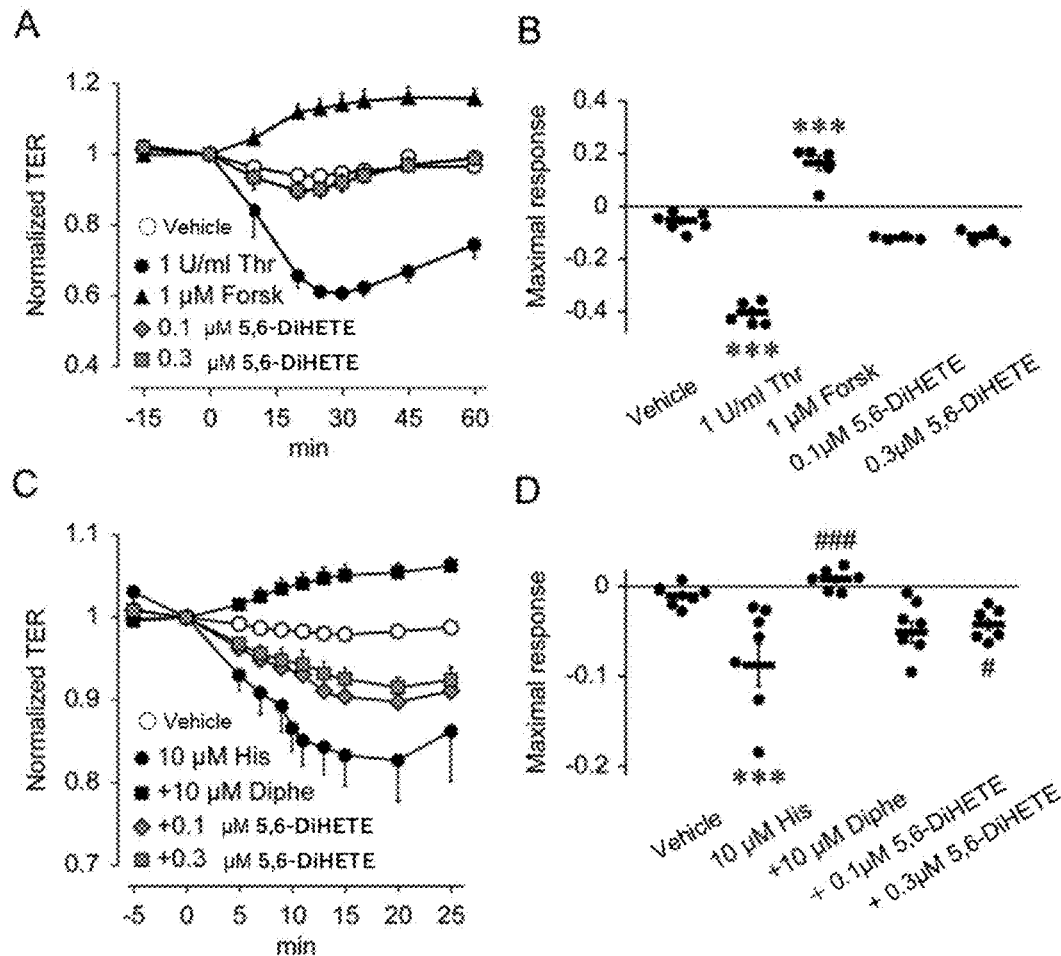
FIG. 4 shows an effect of 5,6-DiHETE on histamine-induced endothelial barrier dysfunction. (A) is a graph indicating an effect of thrombin (Thr, 1 U/mL), forskolin (Forsk, 1 μM) or 5,6-DiHETE (0.1 μM and 0.3 μM) on transendothelial electrical resistance (TER) of HUVECs. The results for 0.1 μM 5,6-DiHETE were almost the same values as those for 0.3 μM 5,6-DiHETE, and thus overlap therewith in the graph. (B) is a graph indicating quantified maximum values of normalized cell indices (n=4 to 7). * represents $P<0.001$ (relative to vehicle). (C) is a graph indicating effects of diphenhydramine (10 μM) pretreatment (+10 μM Diphe) or 5,6-DiHETE (0.1 μM and 0.3 μM) pretreatment (+0.1 μM 5,6-DiHETE and +0.3 μM 5,6-DiHETE) on histamine (His)-induced changes in TER of HUVECs. (D) is a graph indicating quantified maximum values of normalized cell indices (n=8). * represents $P<0.001$ (relative to vehicle), # represents $P<0.05$, and ### represents $P<0.001$ (relative to histamine)

The results were as shown in FIG. 4.

From the results shown in FIGS. 4A and 4B, the treatment with thrombin (1 U/mL) significantly lowered the TER, whereas the treatment with the adenylate cyclase activator forskolin (1 µM) increased the TER. The treatments with 5,6-DiHETE alone (0.1 µM and 0.3 µM) did not change the TER. From the results shown in FIGS. 4C and 4D, the treatment with histamine (10 µM) significantly reduced the TER (minimum of 0.82±0.05-fold), which was abrogated by the pretreatment with the histamine H1 receptor antagonist diphenhydramine (10 µM). Also, the pretreatment with 5,6-DiHETE (0.3 µM, 15 minutes) significantly inhibited the histamine-induced barrier disruption (minimum 0.915±0.012-fold). These results demonstrated that 5,6-DiHETE inhibits the endothelial barrier dysfunction under histamine stimulation.

Example 5: Inhibitory Effect of 5,6-DiHETE on Histamine-Induced eNOS Phosphorylation and NO Production (1) Evaluation of eNOS Phosphorylation To the plates on which the HUVECs were cultured, 5,6-DiHETE was added so as to attain 100 nM, and, 15 minutes after the addition, histamine was added so as to attain 10 µM. Then, in order to measure the protein masses of phosphorylated eNOS and eNOS, 5 minutes after the administration of histamine, the HUVECs were lysed with a modified lysis buffer (50 mM Tris-HCl (pH 7.4), 0.1 mM EDTA, 0.1 mM EGTA, 1% NP-40 substitute, 0.1% SDS, 0.1% deoxycholic acid, 50 mM NaF, 1 mM $Na_3VO_4$, and 10 mM β-glycerophosphate). Pefabloc SC (1.0 mg/mL) and cOmplete Protease Inhibitor Cocktail tablets (1 tablet/50 mL) were added fresh into the lysis buffer. Protein (20 µg) was electrophoresed and blotted onto a PVDF membrane. The membranes were probed using a mouse anti-human phosphorylated eNOS (pS1177, manufactured by BD Transduction Laboratories) antibody or a mouse anti-human eNOS antibody (manufactured by BD Transduction Laboratories) overnight at 4° C. As a secondary antibody, goat anti-mouse IgG IRDye 800CW (manufactured by LI-COR Biosciences) was applied at room temperature for 30 minutes (FIG. 5A). Bands were detected and quantified using an Odyssey system (manufactured by LI-COR Biosciences) (FIG. 5B). Specifically, the bands of phosphorylated eNOS and eNOS were detected by scanning (800 nm) with the Odyssey system, and their intensity (band brightness) was quantified. The phosphorylation level of eNOS (ratio of phosphorylated eNOS to eNOS) was quantified and evaluated by a relative value obtained by dividing the band brightness of phosphorylated eNOS by the band brightness of eNOS. Note that it is known that serine/threonine kinase Akt phosphorylates/activates eNOS to induce NO production (van Nieuw Amerongen, G P et al., Circulation research, 87:335-340 (2000) and Dimmeler, S. et al., Nature, 399: 601-605 (1999)).

(2) Evaluation of NO Generation

The HUVECs were washed three times with HEPES and incubated in HEPES supplemented with 1 mM L-arginine and 10 µM tetrahydrobiopterin. After equilibration for 30 minutes, the medium was exchanged, and the cells were incubated for additional 30 minutes. The cells were subsequently stimulated with 5,6-DiHETE (0.1 µM) or diphenhydramine (10 µM) for 15 minutes and then stimulated with histamine (10 µM) for 5 minutes. In addition, the group not stimulated with any of diphenhydramine, 5,6-DiHETE and histamine was defined as "nonstimulated". The conditioned media before and after the stimulation (100 µL each) were collected and centrifuged in each amount of 300 g for 3 minutes. The supernatants were collected, and used to measure nitrite and nitrate, as stable metabolites of NO, by an ENO-20 NOx analyzer (manufactured by Eicom Corporation). The degrees of increases of nitrite and nitrate levels after the stimulation were normalized with cellular protein contents.

(3) Results

Figure 5:
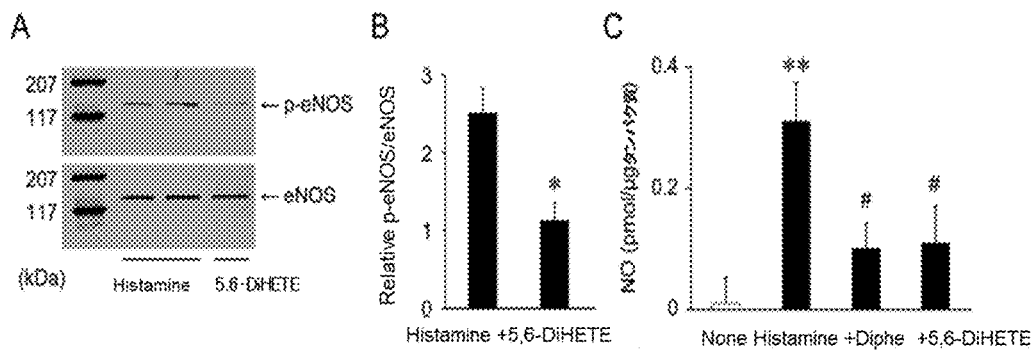
FIG. 5 shows an effect of 5,6-DiHETE on histamine-induced eNOS (Endothelial Nitric Oxide Synthase) phosphorylation and NO production in HUVECs. Effect of pretreatment with 5,6-DiHETE (0.1 µM) on histamine (10 µM)-induced eNOS phosphorylation and NO production. (A) is an image showing representative results of Western blot analysis of total eNOS and phosphorylated eNOS (p-eNOS). (B) is a graph indicating quantified eNOS phosphorylation (n=8). * represents P<0.05 (relative to histamine) (C) is a graph showing an effect of diphenhydramine (Diphe) (10 µM) pretreatment or 5,6-DiHETE (0.1 µM) pretreatment on histamine-induced NO production (n=6 to 10). ** represents P<0.01 (relative to nonstimulated, and # represents P<0.05 (relative to histamine).

The results were as shown in FIG. 5.
The results shown in FIGS. 5A and 5B confirmed that the treatment with histamine (10 µM, 5 minutes) result in eNOS phosphorylation at serine 1177, which is essential for synthesis of NO in HUVECs. Also, the pretreatment with 5,6-DiHETE (0.1 µM, 15 minutes) significantly reduced histamine-induced phosphorylation of eNOS. The results shown in FIG. 5B confirmed that the treatment with 5,6-DiHETE significantly reduces the ratio of phosphorylated eNOS as compared with the administration of histamine alone. From the results shown in FIG. 5C, histamine (10 µM) stimulated NO production (0.31±0.06 pmol/µg protein), which was, however, abrogated by the pretreatment with the histamine H1 receptor antagonist diphenhydramine (10 µM, 15 minutes). Consistent with the results for eNOS phosphorylation, the pretreatment with 5,6-DiHETE (0.1 µM, 15 minutes) significantly inhibited histamine-induced NO production (0.11±0.06 pmol/µg protein). These results demonstrated that 5,6-DiHETE inhibits eNOS phosphorylation and NO production in endothelial cells.

Example 6: Inhibitory Effect of 5,6-DiHETE on Histamine-Induced Increase of Calcium Ion Concentration in Endothelial Cells (1) Measurement of Calcium Ion ($Ca^{2+}$) Concentration HUVECs were incubated with a calcium fluorescence indicator (3 µg fura-2/AM containing 0.11% Cremophor EL) for 30 minutes and washed with an HEPES buffer three times. Next, each reagent was added to the HUVECs so as to attain 10 µM diphenhydramine, 0.03 µM 5,6-DiHETE, 0.1 µM 5,6-DiHETE or 0.3 µM 5,6-DiHETE (pretreatment). Then, 5 minutes after the addition of each reagent, histamine was added so as to attain 10 µM. In addition, a group to which histamine was added so as to attain 10 µM without pretreatment was also prepared. A cover slip was placed in a specialized airtight chamber mounted onto the stage of a microscope maintained at 37° C. The HUVECs were excited at 340 nm and 380 nm and the emitted fluorescence signal was measured every 3 seconds at 510 nm for 60 seconds. The fluorescence ratio (R:F340/F380) was determined using a fluorescence imaging system (AQUACOSMOS, manufactured by Hamamatsu Photonics K.K.). After the experiment, 1 µM ionomycin was added and the fluorescence changes were measured in the presence of 0 or 1.5 mM calcium ions. The calcium ion concentration was indicated as Δ fluorescence ratio. AUC was calculated 1 minute after each stimulus to evaluate the Δ fluorescence ratio. It is known that the increase of calcium ion concentration in endothelial cells promotes NO production by eNOS phosphorylation and expands smooth muscle cells (Garcia-Cardena, G. et al., Nature, 392: 821-824(1998); and Luo, Z. et al., The Journal of clinical investigation, 106: 493-499(2000)).

(2) Results

Figure 6:
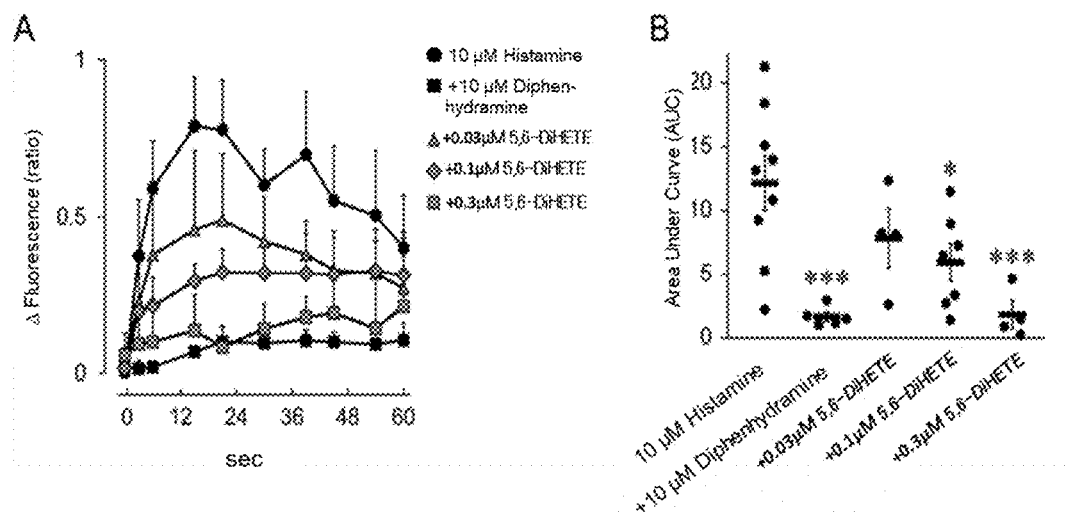
FIG. 6 shows an effect of 5,6-DiHETE on histamine-induced increase of calcium ion concentration in endothelial cells. (A) is a graph indicating histamine-induced changes over time in calcium ion concentration levels in HUVECs and an effect of diphenhydramine pretreatment (+10 µM diphenhydramine) or 5,6-DiHETE pretreatment (+0.03 µM 5,6-DiHETE, +0.1 µM 5,6-DiHETE and +0.3 µM 5,6-DiHETE). (B) is a graph indicating quantification by the area under the curve (AUC) at 1 minute after stimulation. * represents P<0.05, and *** represents P<0.001 (relative to histamine)

The results were as shown in FIG. 6.
From the results shown in FIGS. 6A and 6B, it was confirmed that the treatment with histamine (10 µM) rapidly increased the calcium ion concentration ($[Ca^2\pm]i$) in HUVECs (AUC:12.2±2.1), but that the increase of calcium ion concentration was suppressed (AUC:1.5±0.4) by the pretreatment with the histamine H1 receptor antagonist diphenhydramine (10 µM). Also, it was confirmed that the pretreatment with 0.03 µM 5,6-DiHETE did not inhibit the histamine-induced increase of calcium ion concentration (AUC:7.8±2.3), but that the pretreatments with 0.1 µM and 0.3 µM 5,6-DiHETE significantly inhibited the increase of calcium ion concentration in a dose-dependent manner (AUC:5.9±1.5 and 1.8±1.1, respectively). From the above results, it was demonstrated that 5,6-DiHETE inhibits the increase of calcium ion concentration in endothelial cells.

Example 7: Preparation of Colitis Model Mouse (1) Preparation of Colitis Model Mouse C57BL/6 strain mice (male, 8 to 12 weeks old) were fed with water containing 2% dextran sodium sulfate (manufactured by MP Bio, hereinafter sometimes referred to as "DSS") for 4 days to prepare colitis model mice (hereinafter, sometimes referred to as "colitis group" in Examples 7 to 10). The mice taken with DSS for 4 days were fed with normal water from Day 5. The DSS intake start date was defined as Day 1 of the test, and the day before the DSS intake start date was defined as Day 0 of the test. In addition, a group in which C57BL/6 strain mice (male, 8 to 12 weeks old) were fed with normal water was defined as a "healthy group" (the same applies to Examples 8 to 10).

(2) Evaluation of Colitis Severity

In order to evaluate colitis severity, the fecal condition was evaluated and the body weight was measured daily for the colitis model mice and healthy group prepared in the above item (1). The fecal condition was evaluated based on the following five-grade fecal scores. Specifically, the fecal scores were 0: normal; 1: soft but still formed; 2: very soft; 3: diarrhea; and 4: bloody feces. In addition, the colon length was measured as an index of the colitis severity.

(3) Statistical Processing

In Examples 7 to 10, the measured values were expressed as mean±standard error (SEM). For statistical evaluation of the data, unpaired Student's t-test or one-way analysis of variance (ANOVA) was used, and then Tukey's multiple comparison test was conducted. When p<0.05, there was decided to be a statistically significant difference.

(4) Results

Figure 7:
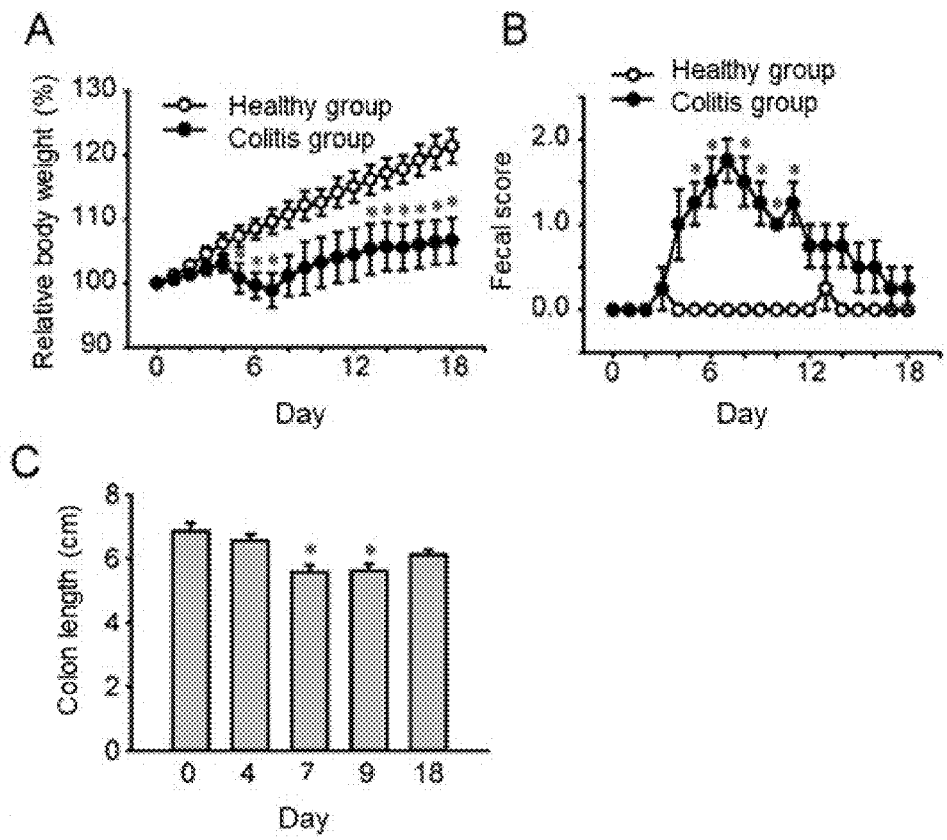
FIG. 7 is a graph indicating the process after induction of colitis in a healthy group or colitis model mice (colitis group). (A) is a graph indicating relative changes in body weights for the colitis group (colitis model mice) (n=4) and the healthy group (n=4). The body weights are expressed as values relative to the percentages of the body weights on Day 0. * represents P<0.05 (relative to healthy group). (B) is a graph indicating changes in fecal scores for the colitis group (colitis model mice) (n=4) and the healthy group (n=4). * represents P<0.05 (relative to healthy group). (C) is a graph indicating the colon lengths (n=4) on Days 0, 4, 7, 9 and 18 for the colitis group (colitis model mice). * represents P<0.05 (relative to Day 0). The measured values are expressed as mean±standard error.

The results of the evaluation performed in the above item (2) on the model mice prepared in the above item (1) were as shown in FIG. 7.

From the results shown in FIG. 7, the body weight increased during the test period in the healthy group, whereas the body weight decreased from Day 4 of the test and increased from Day 7 of the test in the colitis group. In addition, the feces in the healthy group were normal, whereas, in the colitis group, feces were soft (fecal score 1) from the Day 4 of the test, and the fecal condition worsened most on Day 7 of the test (fecal score 1.8±0.3) and gradually recovered from Day 7 of the test. Furthermore, in the colitis group, the colon length was significantly short on Days 7 and 9 of the test (5.6±0.2 cm, respectively) as compared with the colon length on Day 0 of the test (6.9±0.3 cm), and, on Day 18 of the test, the shortening of the colon length recovered. From these results, it was confirmed that the intake of dextran sodium sulfate (DSS) induces colitis so that colitis model mice can be prepared. In addition, the colitis model mice were judged to enter into the healing phase on Day 9 of the test.

Example 8: Fluctuation in Lipid Mediator Concentration in Colitis Model Mouse (1) Measurement of Lipid Mediator Concentration Absolute concentrations of lipid mediators in inflamed colon tissue were measured using liquid chromatography-tandem mass spectrometry (LC-MSMS). The measurement was made with reference to Le Faouder P. et al., Journal of Chromatography. B, Analytical Technologies in the Biomedical and Life Sciences, 932: 123-133(2013). Specifically, an intestinal tissue homogenate was mixed in 200 μL ethanol using vortex for 30 seconds and incubated for 1 hour in the dark at 4° C. After centrifugation at 10,000×g for 15 minutes, 100 μL supernatant mixed with 850 μL distilled water, 10 μL formic acid and 50 μL internal standard mixture (100 ng/mL LTD4-d4 and 12-HETE-d8) was washed with a solid phase extraction cartridge (OASIS HLB, manufactured by Waters), and then washed with 1 mL distilled water and 1 mL hexane. The samples were each eluted with 1 mL ethanol, dried under vacuum and reconstituted in 50 μL ethanol. Ten (10) μL of the sample was injected into an HPLC system with electrospray ionization in cation and anion modes and LC-MS/MS of a triple quadrupole mass spectrometer (LCMS-8030, manufactured by Shimadzu Corporation). Liquid chromatography separation was performed using Inertsil ODS-3 column (manufactured by GL Science Co., Ltd.) using a mobile phase consisting of 0.05% (v/v) formic acid (solvent A) and acetonitrile (solvent B) containing 0.05% (v/v) formic acid. The following gradients were used at a flow rate of 400 μL/min: 95:5 (A:B) at the initial stage (2 minutes), 75:25 for 5 minutes, 65:35 for 10 minutes, 25:75 for 20 minutes and 5:95 for 25 minutes. For analysis, the monitored transition of 5,6-DiHETE was m/z 335.3→145.1, and the elution time was 18 minutes.

(2) Results

Figure 8:
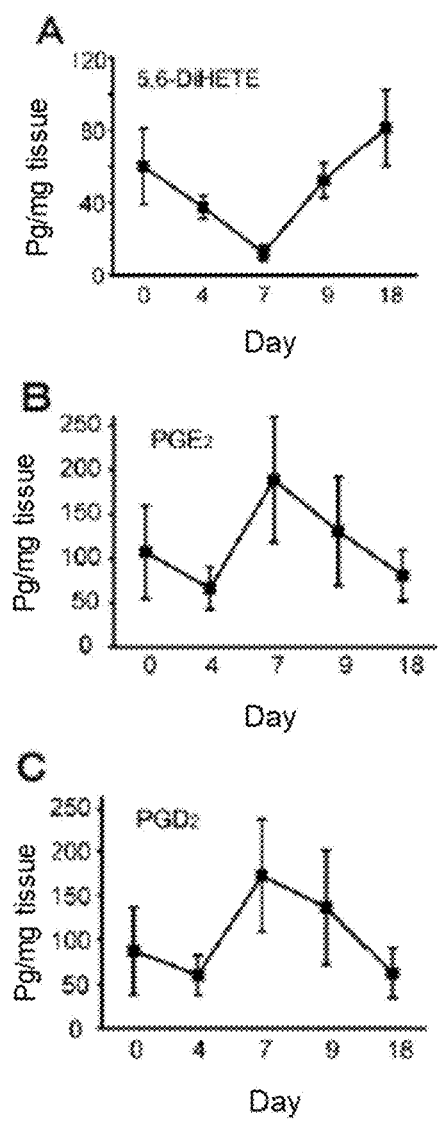
FIG. 8 is a graph indicating an absolute concentration (n=4) of each lipid mediator in the colon. The measured values are expressed as mean±standard error.

The evaluation results were as shown in FIG. 8.

From the results shown in FIG. 8, the absolute concentration of 5,6-DiHETE decreased from Day 0 of the test (60.1±21.0 pg/mg tissue) to Day 7 of the test (12.2±4.2 pg/mg tissue), and then increased during the healing phase, i.e., from Day 9 of the test (52.4±9.6 pg/mg tissue) to Day 18 of the test (81.4±21.0 pg/mg tissue). On the other hand, the absolute concentrations of $PGE_2$ and $PGD_2$, which mediate inflammatory responses, were highest on Day 7 of the test and then decreased during the healing phase. From these results, it was demonstrated that 5,6-DiHETE decreased in the period until Day 7 of the test during which DSS-induced colitis worsened, and increased in the healing phase.

Example 9: Effect of 5,6-DiHETE for Promoting Recovery from Colitis (1) Administration of 5,6-DiHETE To investigate the role of 5,6-DiHETE in the healing phase, the colitis model mice prepared in Example 7(1) were intraperitoneally injected with 5,6-DiHETE (manufactured by Cayman Chemical) (50 μg/kg/day) or HC-067047 (manufactured by Cayman Chemical) (1 mg/kg/day) on Days 9, 11 and 13 of the test (hereinafter, sometimes referred to as "5,6-DiHETE-administered group" and "HC-067047-administered group," respectively, in Examples 9 and 10). HC-067047 is known to inhibit an increase of calcium ion concentration in endothelial cells.

(2) Evaluation of Colitis Severity

The colitis severity was determined according to the index and criteria described in Example 7(2).

(3) Results

Figure 9:
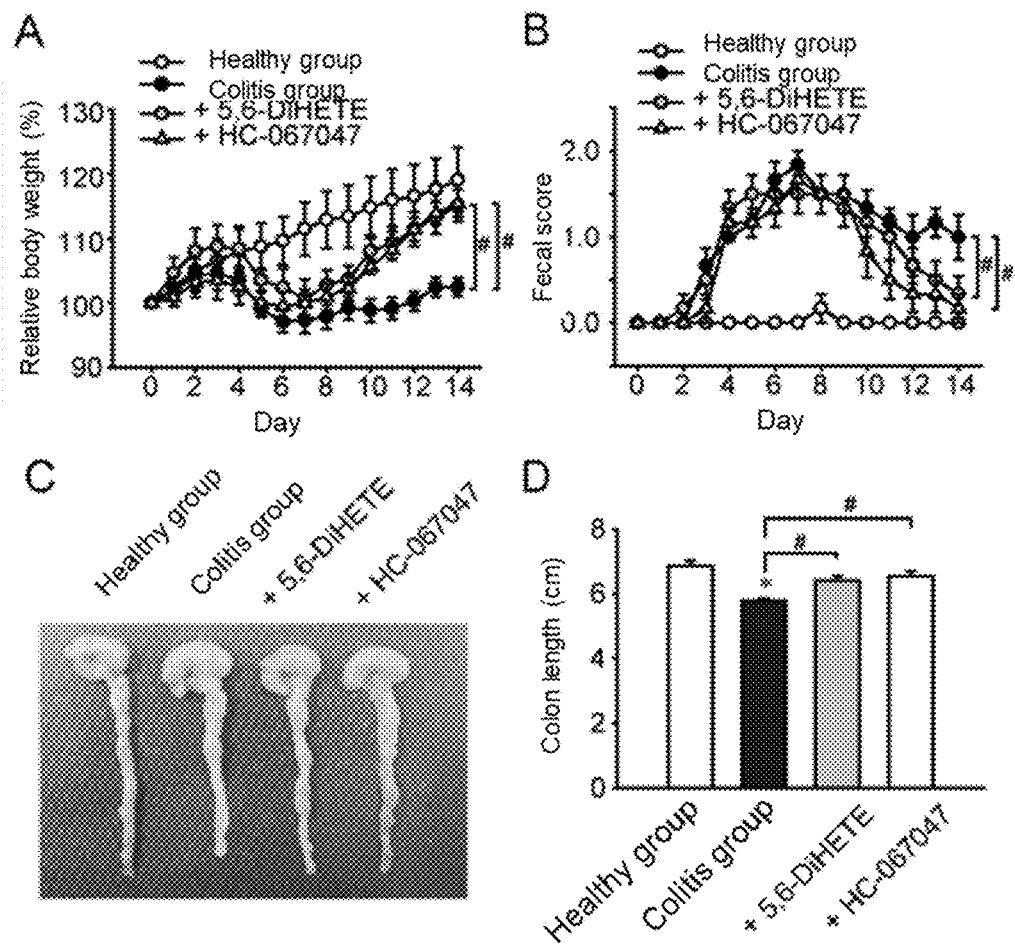
FIG. 9 shows an effect of 5,6-DiHETE on DSS-induced colitis. (A) is a graph indicating relative changes in body weights for the healthy group (n=6), the colitis group (n=6) and a 5,6-DiHETE-administered group (n=6). The body weights are expressed as values relative to the percentages of the body weights on Day 0. # represents P<0.05 (relative to colitis group). (B) is a graph indicating changes in fecal scores for the healthy group (n=6), the colitis group (n=6) and the 5,6-DiHETE-administered group (n=6). * represents P<0.05 (relative to healthy group). (C) is a photograph showing representative mouse colons for the healthy group, the colitis group and the 5,6-DiHETE-administered group. (D) is a graph indicating the colon lengths (n=6) for the healthy group, the colitis group and the 5,6-DiHETE-administered group. # represents P<0.05 (relative to colitis group). The measured values are expressed as mean±standard error.

The results were as shown in FIG. 9.

From the results shown in FIG. 9, the relative body weight on Day 14 of the test was 102.4±1.4% of the initial weight in the colitis group, but increased to 115.2±2.5% of the initial weight in the 5,6-DiHETE-administered group. In addition, in the 5,6-DiHETE-administered group, the fecal score was improved and decreased to the normal level on Day 14 of the test. Furthermore, the colon length on Day 14 of the test was 5.8±0.1 cm in the colitis group, but was 6.4±0.1 cm in the 5,6-DiHETE-administered group. The administration of 5,6-DiHETE suppressed the shortening of the colon. It was confirmed that the HC-067047-administered group was promoted in recovery from colitis as compared with the colitis group. There was no difference in amount of water drunk by each group (data not shown). From the above results, it was demonstrated that the recovery of colitis is promoted by intraperitoneal administration of 5,6-DiHETE to colitis model mice.

Example 10: Inhibitory Effect of 5,6-DiHETE on DSS-Induced Leukocytic Infiltration and Colon Edema (1) Histological Evaluation of DSS-Induced Colitis Distal colon sections on Day 14 of the test in the healthy group, colitis group, 5,6-DiHETE-administered group and HC-067047-administered group were fixed in 4% paraformaldehyde for 24 hours, embedded in paraffin and cut into 2 μm-thick sections. Hematoxylin staining and eosin staining of these sections were performed according to a conventional method. The histologic score was then decided according to the description of Kruschewski M. et al., Digestive Diseases and Sciences, 46: 2336-2343 (2001) to evaluate the colitis severity.

(2) Decision on Colon Edema

The wet/dry weight ratio was used as an index of colon edema (Rachmilewitz D. et al., Gastroenterology, 97: 326-337(1989)). Specifically, the distal colon was collected, and the wet weight was measured. The distal colon was then dried at 60 C for 24 hours, and, thereafter, the dry weight was measured.

(3) Results

Figure 10:
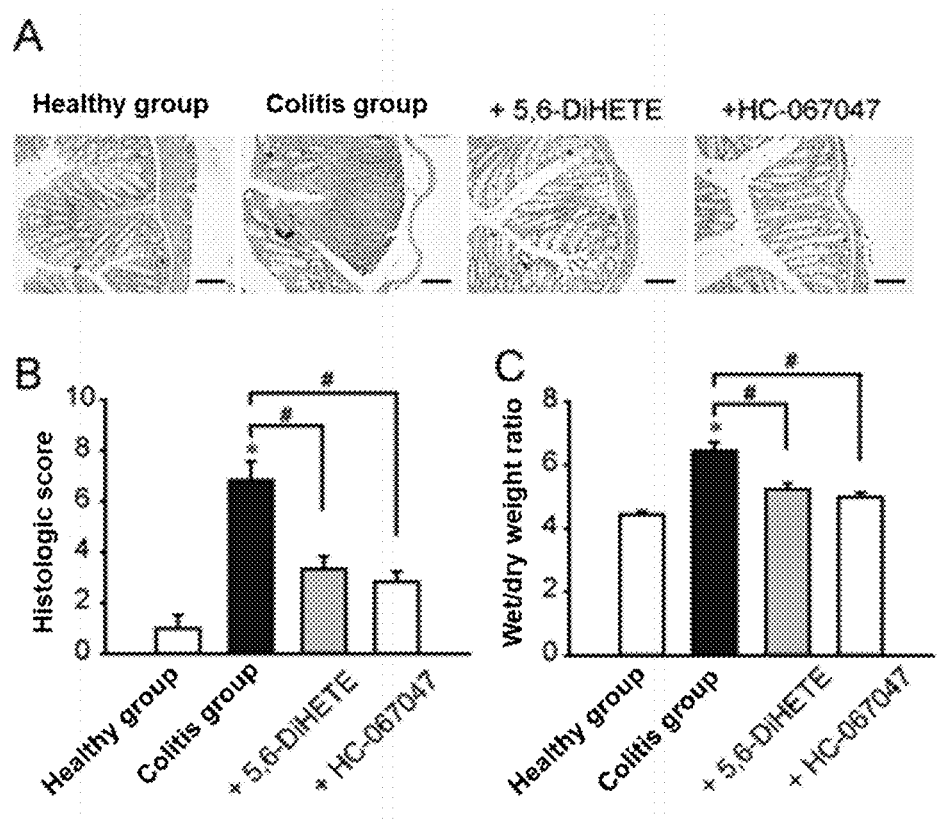
FIG. 10 shows morphological changes in colitis and an effect of 5,6-DiHETE on edema. (A) shows photographs showing morphological appearances of the colons for the healthy group, the colitis group and the 5,6-DiHETE-administered group. The scale bar indicates 100 µm. (B) is a graph indicating histologic scores of colitis (n=6) for the healthy group, the colitis group and the 5,6-DiHETE-administered group. (C) is a graph indicating wet/dry weight ratios (n=4 to 5) for the healthy group, the colitis group and the 5,6-DiHETE-administered group. * represents P<0.05 (relative to healthy group), and # represents P<0.05 (relative to colitis group). The measured values are expressed as mean±standard error.

The results were as shown in FIG. 10.
From the results shown in FIG. 10, on Day 14 of the test, the healthy group showed almost no inflammation in the colon (histologic score: 1.0±0.5). The colitis group showed diffuse leukocytic infiltration, tissue edema and scrotum loss (histologic score: 6.8±0.8), but inflammation in the colon was improved in the 5,6-DiHETE-administered group (histologic score: 3.3±0.5) and the HC-067047-administered group (histologic score: 2.8±0.4). Colon edema was quantitatively evaluated by measuring the water content of the colon tissue. The water content of the colon tissue was 4.4±0.1 in the healthy group, whereas the water content of the colon tissue was 6.4±0.3 in the colitis group, which was indicated to become significantly higher. On the other hand, colon edema was inhibited in the 5,6-DiHETE-administered group and the HC-067047-administered group (5.2±0.2 wet/dry weight ratio and 5.0±0.1 wet/dry weight ratio, respectively). From the above results, it was shown that the recovery of colitis is promoted by intraperitoneal administration of 5,6-DiHETE to colitis model mice.

Example 11: Inhibitory Effect of 5,6-DiHETE on Pneumonia (1) Preparation of Acute Lung Injury Model Mouse Fifty (50) μL of 0.1 N hydrochloric acid was nasally administered to 57BL/6 strain mice (male, 8 to 12 weeks old) to prepare acute lung injury model mice (hereinafter, sometimes referred to as "pneumonia group"). On the other hand, 50 μg/kg 5,6-DiHETE (manufactured by Cayman Chemical) was intraperitoneally administered 5 minutes before and 3 hours after the nasal administration of hydrochloric acid (hereinafter, sometimes referred to as "5,6-DiHETE-administered group").

(2) Histological Evaluation of Pneumonia

The lungs of the pneumonia group and the 5,6-DiHETE-administered group were collected 6 hours after the nasal administration of hydrochloric acid, fixed in 4% paraformaldehyde for 24 hours, embedded in paraffin, and cut into 2 μm-thick sections. Hematoxylin staining and eosin staining of these sections were performed according to a conventional method.

(3) Decision on Pneumonia

The wet/dry weight ratio was used as an index of pulmonary edema (Rachmilewitz D. et al., Gastroenterology, 97: 326-337(1989)). Specifically, 6 hours after the nasal administration of hydrochloric acid, the lungs were collected and the wet weights were measured. The lungs were then dried at 60° C. for 24 hours, and, thereafter, the dry weight was measured. In addition, the ventilatory capacity of the lungs was evaluated as an index of pneumonia using arterial blood oxygen saturations.

(4) Statistical Processing

The measured values were expressed as mean±standard error (SEM). Statistical evaluation of the data was performed using Student's T-test. When $p<0.05$, there was decided to be a statistically significant difference.

(5) Results

Figure 11:
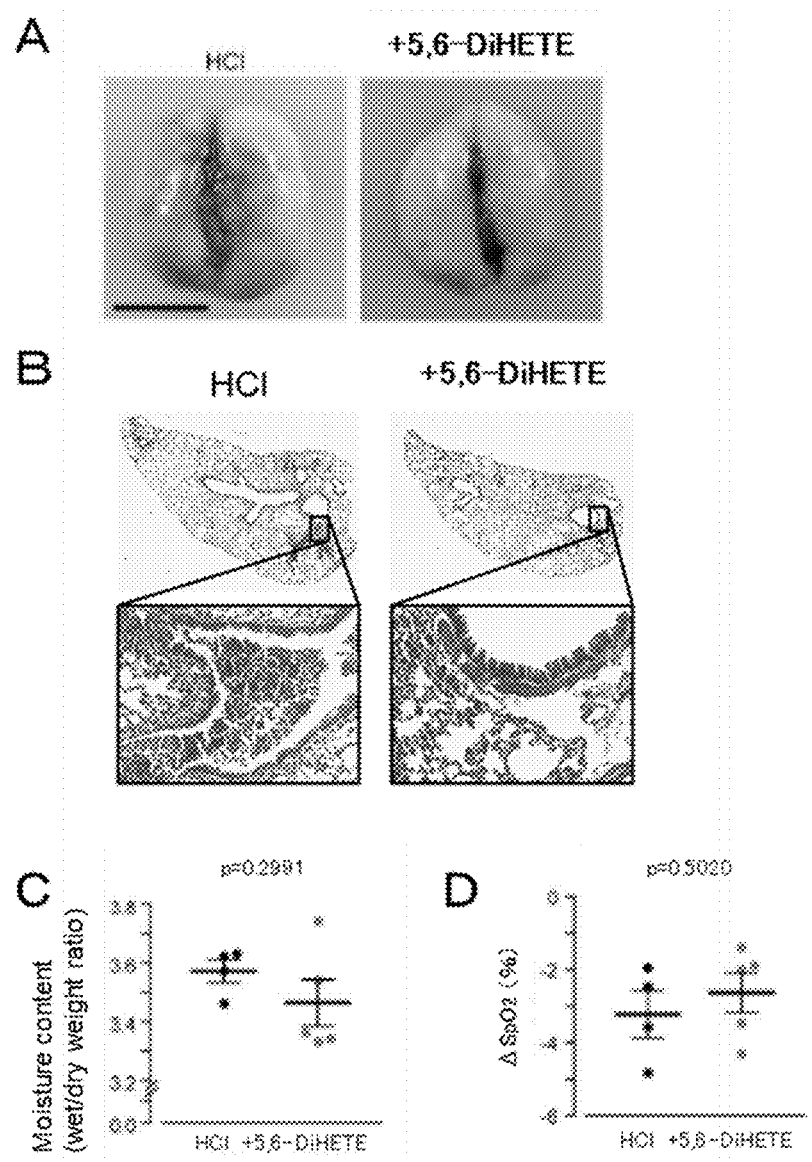
FIG. 11 shows morphological changes in pneumonia and an effect of 5,6-DiHETE on pulmonary edema. (A) shows photographs showing morphological appearances of the lungs for a pneumonia group (HCl) and the 5,6-DiHETE-administered group. (B) shows photographs showing tissue sections of the lungs for the pneumonia group and the 5,6-DiHETE-administered group. (C) is a graph indicating the wet/dry weight ratios (n=4 to 5) for the pneumonia group and the 5,6-DiHETE-administered group. The measured values are expressed as mean±standard error. (D) is a graph indicating arterial blood oxygen saturations (n=4 to 5) for the pneumonia group and the 5,6-DiHETE-administered group. The measured values are expressed as mean±standard error.

The results were as shown in FIG. 11.
From the results shown in FIG. 11, in the appearance of the lungs, the tissue was reddish due to the induction of inflammation in the pneumonia group, but such reddishness was improved in the 5,6-DiHETE-administered group. In addition, the HE-stained image of the lungs showed epithelial damage and neutrophil tissue infiltration in the pneumonia group, but the epithelial damage and neutrophil tissue infiltration were suppressed in the 5,6-DiHETE-administered group. Pulmonary edema, which is a symptom of pneumonia, was evaluated by measuring the moisture content of the lung tissue. Regarding the moisture content of the lung tissue, an increase of moisture content, which indicates tissue edema, was confirmed in the pneumonia group, whereas the moisture content was confirmed to be significantly reduced except one case in the 5,6-DiHETE-administered group. In the pneumonia group, a decrease in arterial blood oxygen saturation, which indicates a decrease in ventilatory capacity of the lungs, was observed, whereas a decrease in arterial blood oxygen saturation was suppressed in the 5,6-DiHETE-administered group. From the above results, it was demonstrated that the recovery of pneumonia is promoted by intraperitoneal administration of 5,6-DiHETE to pneumonia model mice.

Example 12: Inhibitory Effect of 5,6-DiHETE on Anaphylaxis (1) Preparation of Anaphylaxis Model Mouse Histamine (50 mg/kg) lysed in a physiological saline solution was intravenously administered to C57BL/6 strain mice (male, 8 to 12 weeks old) to prepare anaphylaxis model mice (hereinafter, sometimes referred to as "anaphylaxis group"). On the other hand, 15 minutes before the administration of histamine, 50 μg/kg 5,6-DiHETE (manufactured by Cayman Chemical) or 200 mg/kg L-NAME (Sigma) was intravenously administered to the mice (hereinafter, sometimes referred to as "5,6-DiHETE-administered group" or "L-NAME-administered group"). L-NAME is an NO synthesis inhibitor.

(2) Decision on Anaphylaxis

As indices of anaphylactic symptoms, a body temperature decrease and a blood pressure decrease were observed. The body temperature was measured in the rectum every 5 to 30 minutes for 150 minutes using a thermometer (RECTAL PROBE, Physitemp). The blood pressure was measured every 5 to 30 minutes for 150 minutes by the Tail-cuff method using a non-invasive blood pressure measuring device (BP-98A, Softron).

(3) Statistical Processing

The measured values were expressed as mean±standard error (SEM). Statistical evaluation of the data was performed using Student's T-test. When p<0.05, there was decided to be a statistically significant difference.

(4) Results

Figure 12:
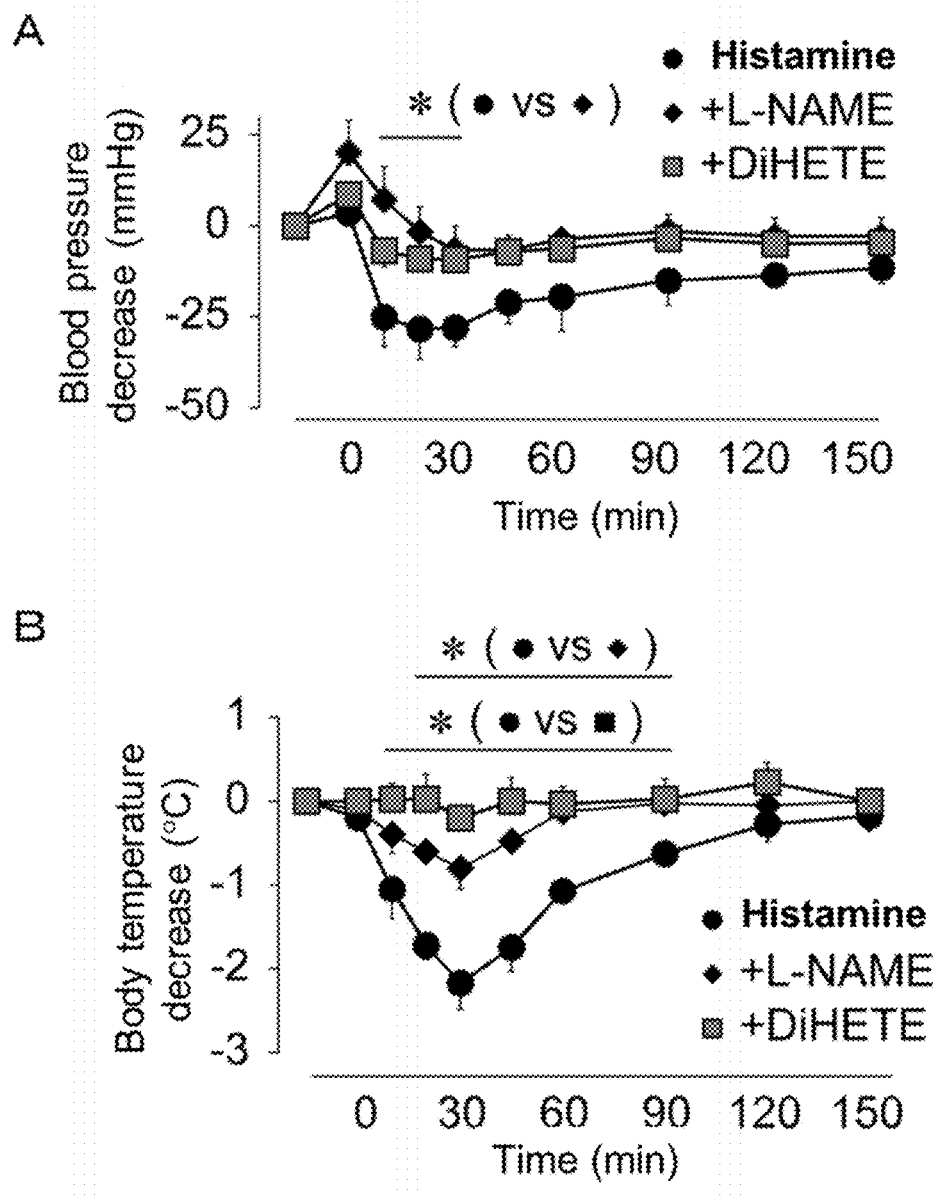
FIG. 12 shows an effect of 5,6-DiHETE on an allergic reaction. (A) is a graph showing the blood pressures for an anaphylaxis group (histamine), the 5,6-DiHETE-administered group and an L-NAME-administered group. * represents P<0.05 (relative to anaphylaxis group). The measured values are expressed as mean±standard error. (B) is a graph indicating body temperatures for the anaphylaxis group (histamine), the 5,6-DiHETE-administered group and the L-NAME-administered group. * represents P<0.05 (relative to anaphylaxis group). The measured values are expressed as mean±standard error.

The results were as shown in FIG. 12.
From the results shown in FIG. 12, when histamine was intravenously administered to mice, anaphylactic reactions such as a blood pressure decrease and a body temperature decrease were observed. The blood pressure decreased most 20 minutes after the histamine treatment (77.4±10 3 mmHg), but the pretreatment with the NO synthesis inhibitor L-NAME significantly suppressed the histamine-induced blood pressure decrease (106.6±8.8 mmHg). In addition, it was confirmed that the histamine-induced blood pressure decrease tended to be suppressed by the pretreatment with 5,6-DiHETE (93.3±4.9 mmHg). The body temperature decreased most 30 minutes after the histamine treatment (−2.2±0.3° C.), but the pretreatment with L-NAME significantly suppressed the histamine-induced body temperature decrease (−0.8±0.2° C.). The pretreatment with 5,6-DiHETE significantly and almost completely suppressed the histamine-induced body temperature decrease (−0.2±0.1° C.). From these results, it was demonstrated that 5,6-DiHETE suppresses the progression of anaphylaxis.

Example 13: Preparation of 5,6-DiHETE from Blue Fish (1) Preparation of 5,6-DiHETE from Blue Fish The muscles, bones, hearts, livers and intestinal tracts were excised from raw sardines, mackerels and horse mackerels. Each of the excised organs was frozen using liquid nitrogen, and the tissue was crushed using ShakeMasterAuto (BMS-A20TP). Then, methanol was added, the mixture was centrifuged, and the supernatant was collected. The supernatant was diluted with distilled water containing 0.1% formic acid to a 30% solution, and (±) 14(15)-DiHET-d11 (1 μg/ml), eicosapentaenoic acid-d5 (10 μg/ml), docosahexaenoic acid-d5 (10 μg/ml) and arachidonic acid methyl ester-d8 (100 μg/ml) which served as internal standard substances were added thereto. Next, each solution was subjected to solid-phase extraction using Oasis HLB 1 cc Vac Cartridge (Waters, Milford, Mass., USA), and the concentration of each lipid in the obtained specimen was measured by mass spectrometer LCMS-8030 (manufactured by Shimadzu Corporation). Liquid chromatography separation was performed using a Kinetex C18 column (Phenomenex) using a mobile phase consisting of 0.1% (v/v) acetic acid (solvent A) and acetonitrile (solvent B). Liquid chromatography-tandem mass spectrometry was performed in a negative ion mode. The eluate was dried and reconstituted with acetonitrile in distilled water.

(2) Statistical Processing

The results of the experiment were expressed as mean±standard error (SEM) (one-way analysis of variance).

(3) Results

The 5,6-DiHETE concentrations of the muscles, bones, hearts, livers, and intestinal tracts of horse mackerels, mackerels and sardines were as follows. In horse mackerels, 5,6-DiHETE was contained at concentrations of 118.98±17.13 ng/g in the liver, 156.14±26.64 ng/g in the intestinal tract, 3.39±2.07 ng/g in the muscle, 27.72±5.17 ng/g in the bone, and 43.95±22.53 ng/g in the heart. In mackerels, 5,6-DiHETE was contained at concentrations of 274.18±54.53 ng/g in the liver, 334.49±205.79 ng/g in the intestinal tract, 22.63±16.13 ng/g in the muscle, 32.00±5.41 ng/g in the bone, and 34.36±7.01 ng/g in the heart. In sardines, 5,6-DiHETE was contained at concentrations of 476.11±175.56 ng/g in the liver, 970.22±221.24 ng/g in the intestinal tract, 83.17±32.76 ng/g in the muscle, 108.89±49.58 ng/g in the bone, and 122.06±17.05 ng/g in the heart. From these results, it was confirmed that the 5,6-DiHETE concentration is relatively low in the muscle, bone and heart of blue fish, relatively high in the liver and intestinal tract, and particularly high in the intestinal tract of sardines.

The invention claimed is:
1. A method for treating, preventing, or improving an inflammatory disease, comprising administering an effective amount of (±) 5,6-dihydroxy-8Z,11Z,14Z,17Z-eicosatetraenoic acid (5,6-DiHETE) or a composition comprising the (±) 5,6-dihydroxy-8Z, 11Z, 14Z, 17Z-eicosatetraenoic acid (5,6-DiHETE) to a subject in need thereof.
2. A method for treating, preventing, or improving an allergic disease, comprising administering an effective amount of (±) 5,6-dihydroxy-8Z,11Z,14Z,17Z-eicosatetraenoic acid (5,6-DiHETE) or a composition comprising the (±) 5,6-dihydroxy-8Z, 11Z, 14Z, 17Z-eicosatetraenoic acid (5,6-DiHETE) to a subject in need thereof.
3. The method according to claim 1, wherein the inflammatory disease is an inflammatory disease due to an increase in calcium concentration of vascular endothelial cells.
4. The method according to claim 1, wherein the inflammatory disease is an inflammatory disease developed in a tissue or organ selected from the group consisting of digestive organs, circulatory organs, respiratory organs, urinary organs, genital organs, brain, skin, eyes, and fat.
5. The method according to claim 1, wherein the inflammatory disease is an inflammatory disease developed in the intestinal tract.
6. The method according to claim 5, wherein the inflammatory disease developed in the intestinal tract is a disease selected from the group consisting of inflammatory bowel disease (IBD), irritable bowel syndrome (IBS) and infectious gastroenteritis.
7. The method according to claim 6, wherein the inflammatory bowel disease (IBD) is a disease selected from the group consisting of ulcerative colitis, Crohn disease, enteric tuberculosis, ischemic colitis, radiation enterocolitis and drug-induced enteritis.

8. The method according to claim 1, wherein the inflammatory disease is an inflammatory disease developed in the lung.

9. The method according to claim 8, wherein the inflammatory disease developed in the lung is a disease selected from the group consisting of pneumonia, pulmonary edema and fibroid lung.

10. The method according to claim 1, wherein said composition is in a dosage form selected from the group consisting of oral administration, percutaneous administration, and intravenous administration.

11. The method according to claim 1, wherein said composition is a food composition.

12. The method according to claim 1, wherein said (±) 5,6-dihydroxy-8Z, 11Z, 14Z, 17Z-eicosatetraenoic acid (5,6-DiHETE) is derived from a food.

13. The method according to claim 2, wherein the allergic disease is an allergic disease due to an increase in calcium concentration of vascular endothelial cells.

14. The method according to claim 2, wherein the allergic disease is a disease selected from the group consisting of urticaria, allergic rhinitis, allergic conjunctivitis, atopic dermatitis, allergic gastroenteritis, food allergy, asthma, bronchial asthma, anaphylaxis and anaphylactic shock.

15. The method according to claim 2, wherein said composition is in a dosage form selected from the group consisting of oral administration, percutaneous administration, and intravenous administration.

16. The method according to claim 2, wherein said composition is a food composition.

17. The method according to claim 2, wherein said (±) 5,6-dihydroxy-8Z, 11Z, 14Z, 17Z-eicosatetraenoic acid (5,6-DiHETE) is derived from a food.

* * * * *